US007351435B2

(12) United States Patent
Wannemacher et al.

(10) Patent No.: US 7,351,435 B2
(45) Date of Patent: Apr. 1, 2008

(54) DEGLYCOSYLATED RICIN TOXIN A-CHAIN VACCINE

(75) Inventors: Robert W. Wannemacher, Frederick, MD (US); John F. Hewetson, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1234 days.

(21) Appl. No.: 09/960,315

(22) Filed: Sep. 24, 2001

(65) Prior Publication Data

US 2003/0180308 A1    Sep. 25, 2003

Related U.S. Application Data

(63) Continuation of application No. 09/523,271, filed on Mar. 10, 2000.

(60) Provisional application No. 60/124,283, filed on Mar. 12, 1999.

(51) Int. Cl.
*A61K 39/00* (2006.01)
*A61K 35/78* (2006.01)

(52) U.S. Cl. ............... 424/731; 424/184.1; 424/278.1; 424/279.1; 530/377; 530/395; 530/403

(58) Field of Classification Search ............. 424/184.1, 424/278.1, 279.1, 731; 530/395, 403, 377
See application file for complete search history.

(56) References Cited

U.S. PATENT DOCUMENTS 5,453,271 A * 9/1995 Lemley et al. ........... 424/184.1
5,626,844 A    5/1997 Lemley et al.

OTHER PUBLICATIONS

Wawrzynczak et al. Int. J. Cancer [1991] 47:130-135.*
Yan, C. et al. Vaccine [1996] 14(11):1031-1038.*
Blakely & Thrope, *Cancer Drug Delivery* 3:189-196 (1986).
Brugsch, *New England Journal of Medicine* 262:1039-1040 (1960).
Compton & Gall, *Medicine Legal Journal* 48:51-62 (1980).
Cookson & Nottingham, *Monthly Review Press*, New York, NY:259-282 (1969).
Fodstad, et al, *Breast Journal Cancer* 34:418-425 (1976).
Foxwell, et al., "The Preparation Of Deglycosylated Ricin By Recombination Of Glycosidase-Treated A- And B-Chains: Effects Of Deglycosylation On Toxicity And In Vivo Distribution" *Biochim. Biophys. Acta* 923:59-65 (1987).
Ghetie & Vitetta, "Recent Developments In Immunotoxin Therapy" *Cancer Drug Delivery* 2:191-198 (1994).
Ghetie & Vitetta, *Curr. Opin. Immunol.* 6:707-714 (1994).
Golde, et al., *Infect. Immun.* 65:882-889 (1997).
Hewetson, et al., "A Formalized Toxoid For Proection Of Mice From Inhaled Ricin" *Vaccine Res.* 4:179-187 (1995).
Lamb, et al, *Eur. J. Biochem.* 148:265-270 (1985).

Lemley & Wright, "Mice Are Actively Immunized After Passive Monoclonal Antibody Prophylaxis And Ricin Toxin Challenge" *Immunology* 76:511-513 (1992).
Lindstrom, et al., "An In Vitro Model For Toxin-Mediated Vascular Leak Syndrome: Ricin Toxin A Chain Increases The Permeability Of Human Endothelial Cell Monolayers" *Blood* 90:2323-2334 (1997).
Lord, et al., *FASEB J.* 8:201-208 (1984).
Lord, et al., "Ricin Cytotoxicity, Biosynthesis And Use In Immunoconjugates" *Prog. Medical Chemical* 24:1-28 (1987).
O'Hare, et al. "Expression Of Ricnin A Chain In *Eschericia Coli*" *FEBS Lett.* 216:8-73 (1987).
Roberts, et al., *J. Biol. Chem.* 15682-15686 (1985).
Soler-Rodriguez, "The Toxicity Of Chemically Deglycosylated Ricin A-Chin In Mice" *J. Immunopharmacol* 14:281-291 (1992).
Soler-Rodriguez, et al., "Ricin A-Chain And Ricin A-Chain Immunotoxins Rapidly Damage Human Endothelial Cells :Implications For Vascual Leak Syndrome" *Exp. Cell. Res.* 206:227-234 (1993).
Thompson, et al., *Bact. Res.* 11:115-145 (1947).
Thorpe, et al., *Eur. J. Biochem.* 147:197-206 (1985).
Underwood, et al., *Immunology* 85:256-261 (1995).
Van Heiningen, F. Ed., *In Molecular Action of Toxins and Viruses*, Amsterdam: Elsevier Biomedical Press: 51-105 (1982).
Vitetta, et al, "Immunotoxins: Magic Bullets Or Misguided Missiles" *Trends Pharmacol. Science* 14:148-154 (1993).
Wawrzynczak, et al., "Comparative Biochemical, Cytotoxic And Pharmacokinetic Properties Of Immunotoxins Made With Native Ricin A Chain, Ricin $A_1$ Chain And Recombination Ricin A Chain" *Int. J. Cancer* 47:130-135 (1991).
Wood, et al, "Preproabrin: Genomic Cloning, Characterization And The Pexpression Of The A-Chain In *Escherichia coli*" *Eur. J. Biochem.* 198:723-732 (1991).
Zajtchuk, R. and R.F. Bellamy Eds., *Textbook of Military Medicine*, Office of the Surgeon General, Department of the Army, USA: 631-642 (1997).
Griffiths G. D. et al., Local and systemic responses against ricin toxin promoted by toxoid or peptide vaccines alone or in liposomal formulations' Vaccine, GB, Butterworth Scientific. Guildford, vol. 16, No. 5, Mar. 1, 1998, pp. 530-535, XP004106967 ISSN: 0264-410X.
Griffiths G. D. et al. Comparison of the quality of protection elicited by toxoid and peptide liposomal vaccine formulations aginst ricin as assessed by markers of inflammation' Vaccine GB, Butterworth scientific. Guildford, vol. 17, No. 20-21, Jun. 4, 1999 pp. 2562-2568, XP004169666 ISSN: 0264-410X.
Lemley Paul V et al., Identification and characterization of a monoclonal antibody that neutralizes ricin toxicity in vitro and in vivo. Hybridoma, vol. 13 No. 5, 1994, pp. 417-421, XP000960308 ISSN: 0272-457X.

* cited by examiner

*Primary Examiner*—Christina Chan
*Assistant Examiner*—F. Pierre VanderVegt
(74) *Attorney, Agent, or Firm*—Elizabeth Arwine

(57) ABSTRACT

The present invention relates to a vaccine comprising deglycosylated ricin toxin A-chain and method for making and using the composition.

9 Claims, 15 Drawing Sheets

FIG. 1

% Survival vs Days post-Exposure

- A-chain
- DG A-chain
- Adjuvant
- Saline

FIG. 2A mg/dl by Immunization (Saline, A-Chain, DG A-Chain, Adjuvant)

- PBS
- Ricin - 30 hr
- Ricin - 14 day

FIG. 2B

Ricin Exposure - 30 hr

[Bar chart: y-axis mg/dl, 0-150; A-Chain ~25 (*), DG A-Chain ~5]

P < 0.05

\* = P < 0.05 (difference from PBS aerosol)
+ = P < 0.05 (difference from saline/adjuvant exposed to ricin aerosol)
S = P < 0.05 (difference between dgRTA and RTA exposed to ricin aerosol)

FIG. 2C

Ricin Exposure - 14 days

[Bar chart: y-axis mg/dl, 0-4; A-Chain ~3.25 (*), DG A-Chain ~1]

P < 0.05

\* = P < 0.05 (difference from PBS aerosol)
+ = P < 0.05 (difference from saline/adjuvant exposed to ricin aerosol)
S = P < 0.05 (difference between dgRTA and RTA exposed to ricin aerosol)

Immunization Dose:
0.15 μg/immunization
- Saline
- Alhydrogel
- Novasomes
- QS-21

Immunization Dose:
0.31 μg/immunization
- Saline
- Alhydrogel
- Novasomes
- QS-21

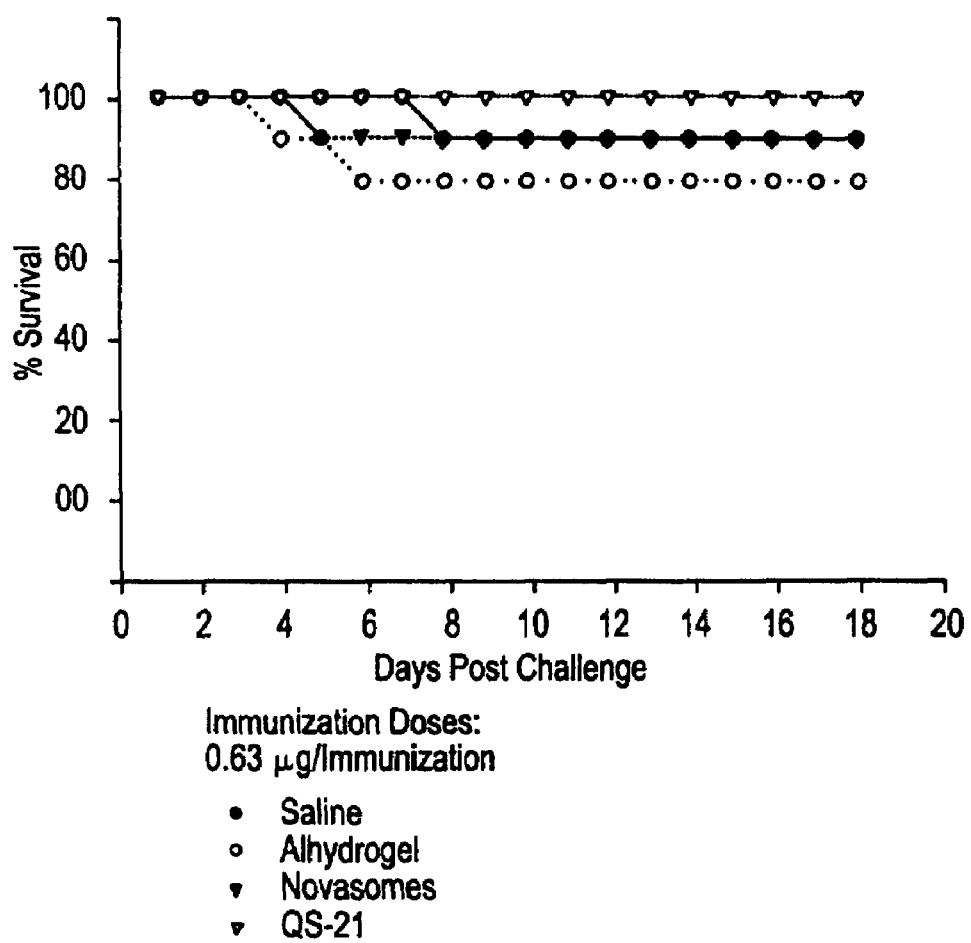

FIG. 7

Survivors (%) vs IV Dose (μg/kg$^{-1}$) of Ricin Toxin D

- ● Control
- ○ Pre-treatment goat anti-ricin IgG

FIG. 8

Cumulative survivors (%) vs Day postexposure 5.0 mg IgG
2.5 mg IgG
0 mg IgG

- 0.5 ml Room Temp.
• 5 ml Room Temp.
♦ 0.5 ml Refrig. Temp.
▲ 5 ml Refrig. Temp.

——— 0.5 ml Room Temp.
— — — 5 ml Room Temp.
— · — 0.5 ml Refrig. Temp.
——— 5 ml Refrig. Temp.

M-Mark 12 Protein Standard
S-2.5μg dgRTA Standard
1-2-μl Precipitate of dgRTA
2-5-μl Precipitate of dgRTA
3-10-μl Precipitate of dgRTA M-SeeBlue Pre-Stained Standard
S-2.5μg dgRTA Standard
1-2-μl Precipitate of dgRTA
1-5-μl Precipitate of dgRTA
1-10-μl Precipitate of dgRTA

DEGLYCOSYLATED RICIN TOXIN A-CHAIN VACCINE

This application is a continuation of U.S. patent application Ser. No. 09/523,271, filed on 10 Mar. 2000, entitled Deglycosylated Ricin Toxin A-Chain Vaccine, naming Robert W. Wannemacher and John F. Hewetson as inventors, which claimed the benefit of priority from U.S. provisional patent application Ser. No 60/124,283, filed on 12 Mar. 1999.

INTRODUCTION

Ricin is an extremely potent toxin (Fodstad et al., 1976, *Br. J. Cancer* 34, 418–425) extracted from the castor bean, *Ricinus communis*, Euphorbiaceae, with an estimated human lethal dose as low as 1 ug/kg. It is a potential biological warfare and terrorist threat to military and civilian personnel. No effective antidote exists for toxic exposure to ricin. It is one of four plant toxins, including abrin, modeccin, and viscumin, that have similar structures and mechanisms of action. Their properties have been reviewed by Olsnes and Pihl (1982, In *Molecular Action of Toxins and Viruses*, F. van Heiningen, Ed., Amsterdam: Elsevier Biomedical Press, pp. 51–105). Ricin remains in the residual mash of castor beans from which oils and other materials have been extracted by cold-pressing seeds of the plant (Brugsch, 1960, *N. Engl. J. Med.* 262, 1039–1040).

Highly purified ricin is commercially available. The toxin is synthesized as a single polypeptide in maturing castor beans where it accumulates in the storage granules of the seeds. The toxin consists of two dissimilar polypeptide chains held together by a disulfide bond that joins cysteinyl residues near the carboxy terminus of the A-chain and the amino terminus of the B-chain. One of these polypeptides (32,000 daltons, designated the A-chain) is a potent inhibitor of protein synthesis. The other (34,000 daltons, the B-chain) is a galactose- or an N-acetylgalactosamine-binding lectin (Lord et al., 1987, *Prog. Med. Chem.* 24, 1–28). All documents cited herein supra or infra are hereby incorporated in their entirety by reference thereto.

When administered parenterally to animals, ricin is highly toxic. The toxic consequences of ricin are attributed to the biologic activity of the A-chain, whereas the B-chain function is to bind the toxin to cell-surface receptors. During endocytosis, the A-chain of ricin is transferred to the cytosol where ribosome inactivation occurs. This results in an inhibition of protein synthesis (Lord et al., 1987, supra). For use as a chemotherapeutic agent, the A-chain has been combined with tumor-specific antibodies to form immunotoxins that are being evaluated in Phase 1 and 2 clinical studies in cancer patients (Vitetta et al., 1993, *Trends Pharmacol. Sci.* 14, 148–154; Ghetie & Vitetta, 1994, *Cancer Drug Delivery* 2, 191–198).

The potential use of biological agents as offensive or terrorist weapons has been reviewed by Franz and Jaax (1997, In *Textbook of Military Medicine*, R. Zajtchuk and R. F. Bellamy, Eds., Office of The Surgeon General, Department of the Army, United States of America, p. 631–642). Because of its relatively high toxicity and its extreme ease of production, ricin toxin (code-named Compound W) was considered for weaponization during the U.S. offensive Biological Warfare Program (Cookson & Nottingham, 1969, New York, N.Y.: Monthly Review Press pp.259–282). Because ricin intoxication is a relatively uncommon occurrence in human medicine, no concerted effort was made to produce specific therapies or prophylactic measures until the early 1990s, when it was perceived to be a significant biological warfare threat. In recent years, ricin toxin has become a favorite tool of extremists who seek to harm others (Franz & Jaax, 1997, supra). Ricin toxin was used in the highly publicized assassination of Bulgarian defector Georgi Markov (Crompton & Gall, 1980, *Med. Leg. J.* 48, 51–62).

When the A-chain of ricin is separated from the B-chain and administered parenterally to animals, it has little or no toxicity (Lord et al., 1987, supra; Soler-Rodriguez et al., 1992, *Int. J. Immunopharmacol.* 14, 281–291). Since the A-chain of ricin contains an epitope that is highly antigenic and induces neutralizing antibodies (Lemley and Wright, 1992, Immunology 76, 511–513), a first vaccine candidate was found in the A-chain of ricin (U.S. Pat. No. 5,453,271 to Lemley et al., Sep. 26, 1995). However, The A-chain of ricin is a glycoprotein that is rapidly cleared from the circulation (Wawrzynczak et al., 1991, *Int. J. Cancer* 47, 130–135) with the liver being the major site of clearance. The rapid clearance of the A-chain reduced its effectiveness as a vaccine.

In an effort to decrease its clearance time, and potentially increase its effectiveness as a vaccine, a deglycosylated A-chain of ricin toxin was used. When the A-chain of ricin toxin is deglycosylated (dgRTA), it is cleared from the circulation at a slower rate than the native chain (Blakey & Thorpe, 1986, *Cancer Drug Deliv.* 3, 189–196; Foxwell et al., 1987, *Biochim. Biophys. Acta* 923, 59–65) resulting in a significantly lower rate of removal by liver as compared to native ricin. In contrast to native ricin, the deglycosylated ricin did not cause histological lesions in the liver and spleen, but its toxicity in rats and mice was elevated by up to fourfold. Thus, destruction of the carbohydrate portion of ricin greatly reduces its clearance by non-parenchymal cells but significantly elevates its toxicity to experimental animals. Therefore, there is a need for a ricin toxin which has a clearance rate adequate to induce protective antibodies, without producing harmful side effects such as lung damage.

SUMMARY OF THE INVENTION

The present invention meets the need discussed above. The present invention relates to a method and composition for inducing an immune response which is protective against intoxication with ricin toxin. In this application we report our results on studies with dgRTA and its use as a vaccine against ricin intoxication.

Because the biological response of the individual to the dgRTA are not known, and whether the antigenic epitope would be lost or interfered with due to the deglycosylation, we evaluated the ability of dgRTA to elicit protective immunity in mice and rats. Our results indicate that dgRTA elicits toxin-neutralizing antibodies in vaccinated animals, and the neutralizing antibodies are detected after two doses of dgRTA vaccine as opposed to three doses of ricin toxin A-chain (RTA). In addition, the dgRTA provided improved protection of lungs in vaccinated rats as compared to RTA-vaccinated animals.

Therefore, it is one object of the present invention to provide a composition comprising deglycosylated ricin toxin A-chain for use as a vaccine against ricin intoxication. The composition is provided in an amount sufficient to induce an immune response in a subject, in conjunction with a physiologically acceptable vehicle and may optionally include an adjuvant to enhance the immune response of the subject.

It is another object of the present invention to provide a method for inducing a protective immune response in a subject against ricin intoxication, comprising administering to a subject deglycosylated ricin toxin A-chain in a pharmaceutically effective amount, in a pharmaceutically effective diluent.

BRIEF DESCRIPTION OF THE DRAWINGS

These and other features, aspects, and advantages of the present invention will become better understood with reference to the following description and appended claims, and accompanying drawings where:

FIG. 1 shows survival of rats vaccinated with RTA or dgRTA.

FIGS. 2 A, B, and C shows bronchioalveolar lavage (BAL) albumin content in rats vaccinated with RTA or dgRTA.

FIG. 7 shows survival of mice immunized with goat anti-ricin IgG and challenged intravenously with increasing doses of ricin toxin D.

FIG. 8 survival of mice passively immunized with goat anti-ricin IgG and challenged with lethal doses of aerosolized ricin toxin.

DETAILED DESCRIPTION

Figure 3:
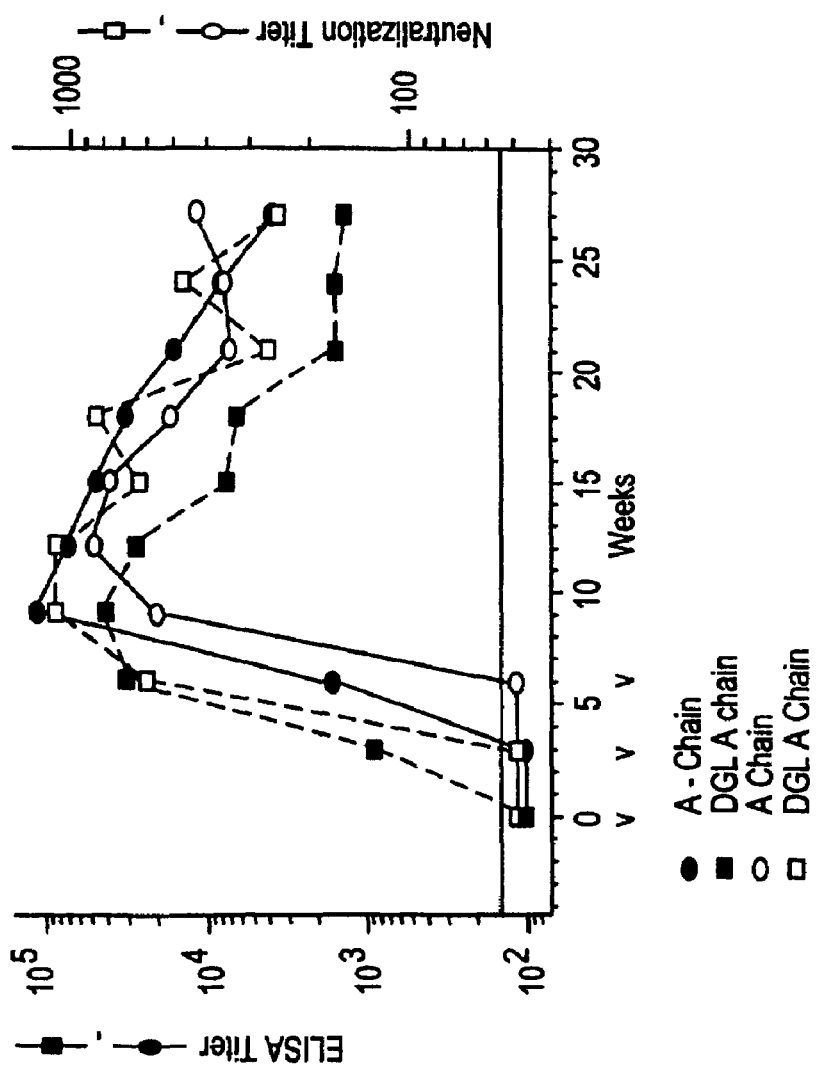
FIG. 3 shows antibody responses in rats vaccinated with RTA or dgRTA.

In one embodiment, the present invention relates to a composition comprising deglycosylated ricin toxin A-chain. Ricin toxin is extracted from the residual mash of the crushed castor bean, *Ricinus communis*, Euphorbiaceae. The toxin consists of two dissimilar polypeptide chains held together by a disulfide bond that joins cysteinyl residue near the carboxy terminus of the A-chain and the amino terminus of the B-chain. By deglycosylated ricin A-chain is meant any ricin A-chain having modified carbohydrate moeities such that the in vivo rate of clearance of the deglycosylated, or modified, ricin A-chain is reduced.

The deglycosylated ricin toxin A-chain described in the examples below was obtained from chemically deglycosylated ricin D toxin. Deglycosylated ricin toxin A-chain can be obtained from other ricin toxins, such as ricin E for example (please see Lord et al., 1987, supra for a discussion of other ricin toxins). Deglycosylation of ricin can be achieved by oxidative cleavage of the ring structure of carbohydrate moieties and subsequent reduction of the resulting aldehyde groups to stable primary alcohols. For example, please see, Thorpe et al., 1985, *Eur. J. Biochem.* 147, 197–206, for a method of deglycosylating ricin A chain. More specifically, and as described below, this can be accomplished by treating the toxin with a mixture of sodium metaperiodate and sodium cyanoborohydride at pH 3.5 for 1 hour at 4° C. (Thorpe et al., 1985, supra). Depending on the incubation time, this procedure can result in destruction of about 50% of the mannose and most fructose residues present on the RTA, whereas the N-acetylglucosamine and most of the xylose residues are unaffected (Vetetta and Thorpe, 1985, supra).

Other methods for removing the mannose and fucose are known to those with ordinary skill in the art.

After deglycosylation, the deglycosylated ricin is split into A and B chains and the B-chain removed. This can be done by using a reducing agent such as 2-mercaptoethanol. For example, the deglycosylated ricin is bound to an acid-treated sepharose 4B column and then split on the column into A and B chains with 2-mercaptoethanol. Deglycosylated A-chain is then eluted with 0.05M borate-NaCl buffer containing 2-mercaptoethanol. Subsequent to elution from the Sepharose 4B column, the dgRTA is dialyzed against 0.005M phosphate buffer (pH 6.5) with DTT and galactose, and the contminating B chain removed. Contaminating B-chain can be removed by immunoprecipitation, for example. The percentage of modified dgRTA that binds to ConA-Sepharose in 0.01 M lactose is a funtion of the amount of mannose destruction (Thorpe et al., 1985, *Eur. J. Biochem.*147, 197–206; Blakey and Thorpe, 1986, Cancer Drug Delivery 3, 189–196).

Thus, chemically modified RTA that had a >90% non-retention on ConA-Sepharose was considered to have had about 50% of the mannose and most of the fucose destroyed by this procedure.

The deglycosylated ricin A-chain can be produced by other methods, for example, molecular methods where a polypeptide having an amino acid sequence encoding the A-chain of ricin, or a portion thereof wherein the portion consists of at least 2–5 amino acids, preferably at least 8–10 amino acids, and more preferably at least 11–15 amino acids, or which is immunologically identifiable with a ricin A-chain can be used to produce a deglycosylated A-chain. A nucleotide sequence or DNA fragment encoding such a recombinant protein, can be cloned into an expression vector and the protein can be expressed in vivo in a host. Please see *Current Protocols in Molecular Biology*. Frederick M. Ausubel et al. (eds.), John Wiley and Sons, Inc. for methods of cloning and expressing a protein in a host cell. The nucleotide sequence for ricin is known (Lamb et al., 1985, *Eur. J. Biochem.* 148, 265–270; Lord, et al., 1984, *FASEB J.*

8, 201–208; O'Hare et al., 1987, *FEBS Lett.* 216, 8–73; Roberts, et al., 1985, *J. Biol. Chem.* 15682–15686; Wood, et al., 1991, *Eur. J. Biochem.* 198, 723–732). The protein can further be fused to other sequences for increasing antigenicity or for ease of purification of the expressed fusion protein. The recombinant or fusion protein can be produced by methods which include culturing the above-described host cells under conditions such that the DNA fragment is expressed and the recombinant or fusion protein is produced thereby. The recombinant or fusion protein can then be isolated using methodology well known in the art. The recombinant or fusion protein can be used as a vaccine for immunity against intoxication with ricin toxin. Expression of the ricin in bacterial cells which cannot glycosylate expressed proteins would be preferable and would result in a ricin toxin A-chain or fragment thereof devoid of carbohydrates. Also related to the present invention are organic or inorganic analogues of the deglycosylated ricin A-chain described above which are designed by computer modeling, synthetically or naturally produced, such that the function of the analogue mimics that of the dgRTA.

In another embodiment, the present invention relates to antibodies specific for the above-described dgRTA. For instance, an antibody can be raised against the dgRTA of the present invention or against a portion thereof of at least 10 amino acids, preferably, 11–15 amino acids, or an immunologically identifiable portion thereof. Persons with ordinary skill in the art using standard methodology can raise monoclonal and polyclonal antibodies to the protein (or polypeptide) of the present invention, or a unique portion thereof. Materials and methods for producing antibodies are well known in the art (see for example Goding, In *Monoclonal Antibodies: Principles and Practice*, Chapter 4, 1986).

In a further embodiment, the present invention relates to a method of detecting the presence of antibodies against dgRTA in a sample. Using standard methodology well known in the art, a diagnostic assay can be constructed by coating on a surface (i.e. a solid support for example, a microtitration plate, a membrane (e.g. nitrocellulose membrane) or a dipstick), all or a unique portion of any of the dgRTA described above, and contacting it with the serum of a person or animal suspected of having ricin intoxication. The presence of a resulting complex formed between the dgRTA and serum antibodies specific therefor can be detected by any of the known methods common in the art, such as fluorescent antibody spectroscopy or colorimetry. This method of detection can be used, for example, for the diagnosis of ricin intoxication and for determining the degree to which an individual has developed anti-ricin antibodies after administration of a vaccine.

In yet another embodiment, the present invention relates to a method for detecting the presence of ricin toxin in a sample. Antibodies against dgRTA can be used for diagnostic assays. Using standard methodology well known in the art, a diagnostic assay can be constructed by coating on a surface (i.e. a solid support, for example, a microtitration plate or a membrane (e.g. nitrocellulose membrane)), antibodies specific for any portion of dgRTA described above, and contacting it with serum or a tissue sample of a person suspected of having ricin intoxication. The presence of a resulting complex formed between the ricin in the serum and antibodies specific therefor can be detected by any of the known methods common in the art, such as fluorescent antibody spectroscopy or colorimetry. This method of detection can be used, for example, for the diagnosis of ricin intoxication. In another embodiment, the present invention relates to a method of protecting a subject from ricin intoxication by administering to said subject an effective amount of antibodes against dgRTA as described above. Also, the present invention relates to a method of reducing ricin intoxication symptoms in a patient by administering to said patient an effective amount of antibodies against dgRTA as described above keepin in mind that the toxin acts rapidly, within 12–24 hours post-intake.

Administration for protection or prophylaxis can be intradermal, intramuscular, or intravenous. When providing a patient with antibodies, the dosage of administered agent will vary depending upon such factors as the patient's age, weight, height, sex, general medical condition, previous medical history, etc. In general, it is desirable to provide the recipient with a dosage of the above compounds which is in the range of from about 1 pg/kg to 10 mg/kg (body weight of patient), although a lower or higher dosage may be administered. Such subjects include all mammals, avian and fish.

In another embodiment, the present invention relates to a diagnostic kit which contains dgRTA described above and ancillary reagents that are well known in the art and that are suitable for use in detecting the presence of antibodies in serum or a tissue sample. Tissue samples contemplated can be from all mammals, plants, avian and fish.

In another embodiment, the present invention relates to a ricin toxin vaccine comprising dgRTA as described above. Vaccine formulations of the present invention comprise an immunogenic amount of a dgRTA in a pharmaceutically acceptable carrier. An "immunogenic amount" is an amount of the dgRTA sufficient to evoke an immune response in the subject to which the vaccine is administered. An amount of from about 0.01–100 ug/kg, preferably 0.05–50.0 ug/kg, preferably 0.1–10 ug/kg, preferably 0.15–10 ug/kg, preferably 0.5–10 ug/kg, preferably 1.0–10 ug/kg, preferably 2.5–10 ug/kg, preferably 5–10 ug/kg, per dose is suitable, depending upon the age and species of the subject being treated. The subject may be inoculated 1–4 times, preferaby 2 times. The vaccine formulations should provide a quantity of dgRTA sufficient to effectively protect the patient against serious or life-threatening ricin intoxication. Exemplary pharmaceutically acceptable carriers include, but are not limited to, sterile pyrogen-free water and sterile pyrogen-free physiological saline solution.

Administration of the dgRTA disclosed herein may be carried out by any suitable means, including parenteral injection (such as intraperitoneal, subcutaneous, or intramuscular injection), in ovo injection of birds, orally, or by topical application of the compound (typically carried in a pharmaceutical formulation) to an airway surface. Topical application of the dgRTA to an airway surface can be carried out by intranasal administration (e.g., by use of dropper, swab, or inhaler which deposits a pharmaceutical formulation intranasally). Topical application of the dgRTA vaccine to an airway surface can also be carried out by inhalation administration, such as by creating respirable particles of a pharmaceutical formulation (including both solid particles and liquid particles) containing the dgRTA as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The vaccine may be given in a single dose schedule, or preferably a multiple dose schedule in which a primary course of vaccination may be with 1–10 separate doses, preferably 2–4 separate doses, preferably 2 separate doses, followed by other doses given at subsequent time intervals required to maintain and or reinforce the immune response, for example, at 1–4 months for a second dose, and if needed, a subsequent dose(s) after several months. Examples of suitable immunization schedules include: (i) 0, 1 months and 6 months, (ii) 0, 7 days and 1 month, (iii) 0 and 4 weeks, (iv) 0 and 6 months, or other schedules sufficient to elicit the desired immune responses expected to confer protective immunity, or reduce disease symptoms, or reduce severity of disease. Levels of induced immunity can be monitored by measuring amount of neutralizing secretory and serum antibodies, and dosages adjusted or vaccinations repeated as necessary to maintain desired levels of protection.

For vaccine use, the dgRTA of the invention can be used directly in vaccine formulations, or lyophilized, as desired, using lyophilization protocols well known to the artisan. Lyophilized dgRTA will typically be maintained at about 4° C. When ready for use the lyophilized dgRTA is reconstituted in water, or if necessary, in a stabilizing solution, e.g., saline or comprising $Mg^{++}$, benzyl alcohol and preferably in a non-polar miscible solvent which is acceptable for vaccine use, such as PEG, with or without adjuvant, as further described below.

The dgRTA composition may be introduced into a host, particularly humans, with a physiologically acceptable vehicle and/or adjuvant. Useful vehicles are well known in the art, and include, e.g., water, buffered water, 0.4% saline, 0.3% glycine, hyaluronic acid and the like. The resulting aqueous solutions may be packaged for use as is, or lyophilized, the lyophilized preparation being rehydrated prior to administration, as mentioned above. The compositions may contain pharmaceutically acceptable auxilliary substances as required to approximate physiological conditions, such as pH adjusting and buffering agents tonicity adjusting agents, wetting agents and the like, for example, sucrose, sodium acetate, sodium lactate, sodium chloride, potassium chloride, calcium chloride, sorbitan monolaurate, triethanolamine oleate, and the like.

In some instances it may be desirable to combine the dgRTA vaccine of the invention with vaccines which induce protective responses to other agents as long as the additional agent vaccine does not increase the side effects or inhibit the production of an effective immune response to dgRTA.

The following examples are included to demonstrate preferred embodiments of the invention. It should be appreciated by those of skill in the art that the techniques disclosed in the examples which follow represent techniques discovered by the inventors and thought to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The primary animal models used to test ricin vaccine candidates were the rat and the mouse. The clinical signs exhibited by rats and mice after exposure to lethal quantities of aerosolized ricin are variable but include a progression of "scruffy" appearance of the hair coat, hunched posture, anorexia, conjunctivitis, and dyspnea. Nonhuman primates exhibit an abrupt onset of rapidly progressive dyspnea 20–24 hours post-exposure to aerosolized ricin. Death, which occurs 2–3 days post-exposure, is attributable to severe respiratory compromise in all three species.

The pathology produced by exposure to aerosolized ricin is similar among mice, rats, and nonhuman primates. Pathologically significant changes are generally confined to the respiratory tract, with the most profound changes observed in the lungs. Principal morphologic features are necrotizing bronchitis, bronchiolitis, alveolitis with suppurative inflammatory infiltrates, edema characterized by marked expansion of the peribronchovascular interstitium, alveolar flooding, intra-alveolar fibrin deposition, and vascular leucocytosis with margination and diapedesis. Ultrastructural studies revealed that type II pneumocytes appeared to be the principal target cell at the alveolar level, but fibroblast and endothelial degeneration was also observed in alveolar septa.

RAT MODEL: The rat model consisted of Fischer rats (F344) (250–275 g) obtained from the Charles River Breeding Laboratories. The animals (20/group) were vaccinated at 0, 3, and 6 weeks with 10 ug administered IM of either RTA or dgRTA formulated with aluminum hydroxide (Alhydrogel™) as an adjuvant. Other groups of rats were injected IM with either adjuvant alone or saline alone as negative controls. The rats were challenged with eight $LD_{50}$ of aerosolized ricin 3 weeks following the last injection at 6 weeks. Fourteen-day survival is shown in FIG. 1. All RTA and dgRTA vaccinated rats survived but the controls died within 3 days of challenge.

At 30 hours or at 14 days following challenge (10 rats/time period), surviving rats in each treatment group were euthanized following bronchoalveolar lavage (BAL) for histologic examination of their lung tissue. The content of albumin in the BAL fluid is shown in FIG. 2.

An elevation in the albumin concentration in the BAL fluid is a biochemical marker of lung injury. At 30 hours post-ricin exposure, the albumin content of BAL fluid from rats given RTA and dgRTA was reduced significantly (75%–90%) compared to that in control rats given the aluminum hydroxide adjuvant or saline. At 30 hours and 14 days post-exposure, the albumin content of BAL fluid from the dgRTA group was significantly lower than that of the RTA group. Findings from the necropsied animals euthanized 30 hours after aerosolized ricin challenge revealed severe histopatholic lesions in the lungs of rats injected with adjuvant or saline that included (1) airway and alveolar epithelial necrosis; (2) edema-expansion of the peribronchovascular interstitium, and alveolar flooding with high fibrin content; (3) suppurative inflammatory infiltrates; (4) vascular leukocytosis with margination and diapedesis; and (5) occasional hemorrhage. Significant pathologic findings were limited to the respiratory tract, and death was attributed to severe respiratory compromise. In contrast, lungs from rats vaccinated with dgRTA or RTA had attenuated necrosis of airways and alveolar epithelial surfaces with little or no edema. Necrotic lesions in the lungs 14 days post-challenge were resolving in animals vaccinated with dgRTA or RTA.

Available data on immune responses to the three-dose schedule of RTA- or dgRTA-vaccinated rats (10/group) are shown in FIG. 3. Mean ELISA antibody titers over $1 \times 10^2$ were observed after a single vaccination with dgRTA. In contrast, two vaccinations with RTA were required to achieve comparable titers. Similar peak titers were observed after two vaccinations with dgRTA and three vaccinations with RTA. Maximum ELISA antibody titers were observed 3 weeks after the last vaccination with dgRTA or RTA. Neutralizing antibodies were detectable after two vaccinations with 10 ug of dgRTA, but three vaccinations were required to detect neutralizing antibodies with RTA. Maximum neutralizating antibody titers were observed 3 to 4 weeks after the last vaccination with RTA or dgRTA. The earlier appearance of antibodies, as measured by ELISA and by toxin neutralization, and the better lung protection in rats vaccinated with dgRTA as compared with RTA suggested that dgRTA might be the better candidate as a ricin toxin vaccine.

EXAMPLE 2

MOUSE MODEL:CD-1 VAF plus mice (20–25 grams) obtained from Charles River Breeding Laboratories were used (1) to conduct dose-ranging studies of dgRTA, (2) to compare the efficacy of two (0 and 3 weeks) or three (0, 3, and 6 weeks) IM injections with various concentrations of either RTA or dgRTA in saline, and (3) to compare the effect of adjuvants with dgRTA.

Figure 4:
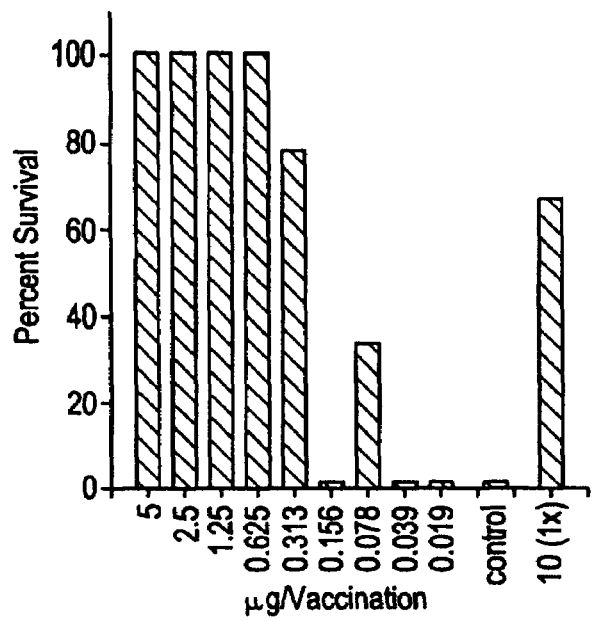
FIG. 4 shows dose escalation study on survival after aerosol ricin toxin exposure in mice vaccinated with dgRTA.

For the dose escalation study, 10 mice per group were vaccinated with two IM doses of dgRTA at 0 and 3 weeks and were challenged 3 weeks later with 2.2 $LD_{99}$ of aerosolized ricin toxin. Fourteen-day survival results are shown in FIG. 4. All mice vaccinated with 0.625, 1.25, 2.5, or 5 ug of dgRTA survived 14 days following the aerosol challenge. Based on this study, a 10-ug vaccination dose, at least 10 times the minimal protective dose, was used for further studies on the number of doses and the effectiveness of various adjuvants in protecting mice against lethal ricin aerosol challenge.

Figure 5:
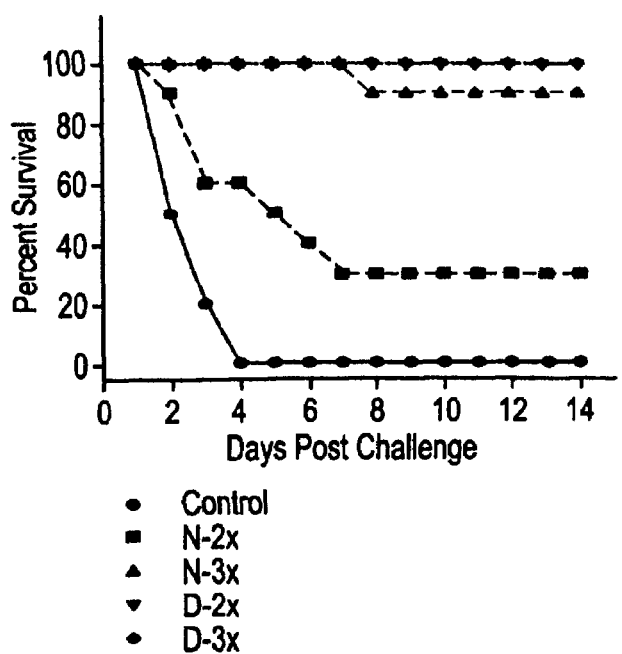
FIG. 5 shows survival of mice vaccinated with two or three doses of RTA (N) or dgRTA (D) and challenged with lethal doses of aerosolized ricin toxin.

In the vaccine efficacy study, 3 weeks following the last vaccination with 10 ug of dgRTA in saline, 10 mice per group were challenged with 2.6 $LD_{99}$ of aerosolized ricin toxin. Survival is shown in FIG. 5. Control mice dosed with saline died by day 4 following challenge with aerosolized ricin toxin. All mice vaccinated with two doses of dgRTA survived for 14 days, but only 30% of the mice vaccinated with two doses of RTA survived the challenge. All mice vaccinated with three doses of dgRTA and 90% of mice vaccinated with three doses of RTA survived for 14 days. These results confirm the findings in the rat model that dgRTA is a better vaccine candidate than RTA in protecting against ricin intoxication and provide the rationale for the selection of dgRTA as a ricin toxin vaccine candidate.

Figure 6A:
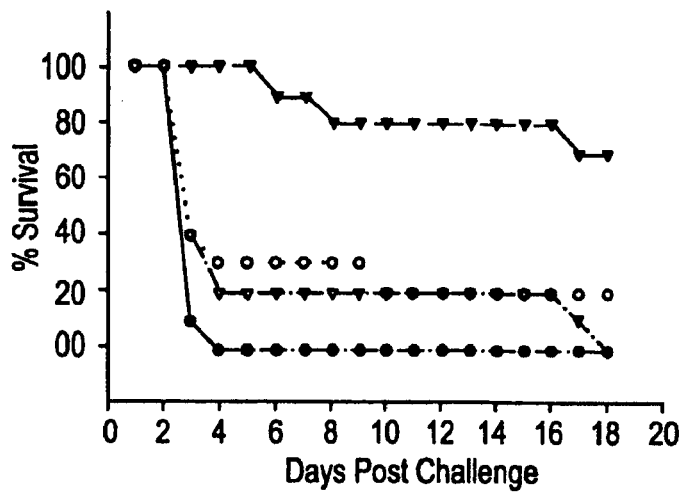
FIGS. 6, A, B, and C show adjuvant effect on survival of dgRTA vaccinated mice exposed to aerosolized ricin toxin vaccinated with 0.15 ug(A), 0.31 ug (B), and 0.63 ug (C) of dgRTA/immunization.
Figure 6B:
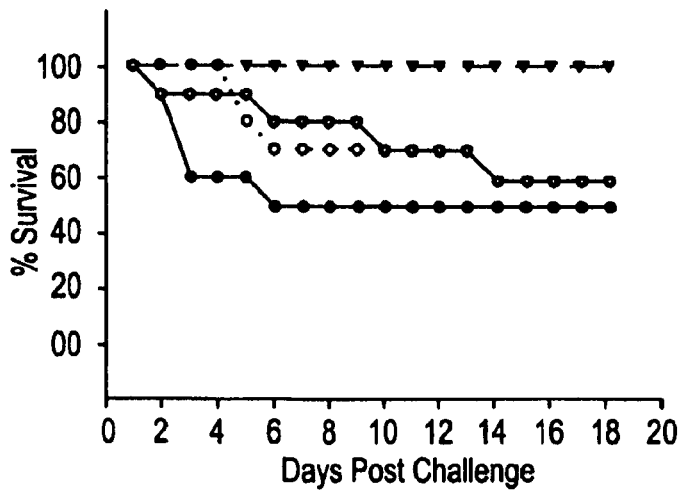

Three adjuvants (aluminum hydroxide [Alhydrogel™], Novasomes, and QS-21) were evaluated for their effects on dgRTA protection against aerosolized ricin toxin. Three months following the last immunization, mice were challenged with 2.5 $LD_{99}$ of aerosolized ricin toxin. Fourteen-day survival results are shown in FIG. 6. Neither aluminum hydroxide nor QS-21 significantly improved survival of mice vaccinated with 0.15, 0.31, or 0.63 ug of dgRTA. In contrast, Novasomes significantly improved survival of mice vaccinated with 0.15 or 0.31 ug of dgRTA, but not with 0.63 ug of dgRTA. Since Novasomes are not approved for parenteral human use, dgRTA vaccine was formulated without an adjuvant.

EXAMPLE 3

Early in the ricin vaccine development program, a proof of concept for at least one component of an aerosol efficacy model was established. Studies were performed to determine if goat antibodies raised to ricin toxoid would protect unvaccinated mice from lethal ricin challenge. Goats were vaccinated with ricin toxoid (BB-IND 6181) and plasmapheresed when their sera contained high titers (>10,000) of anti-ricin toxin IgG. The goat IgG was purified and used in passive antibody protection studies. Groups of five CD1 mice were injected IV with 100 ug of purified goat anti-ricin toxin IgG (FIG. 7).

The control group received 100 ug of normal goat IgG. Within 15 minutes, each group was challenged IV with ricin toxin D at doses ranging from 20–200 ug/kg$^{-1}$ (2 to 20 $LD_{50}$). All mice in the control group died at a ricin toxin dose of 20 ug/kg$^{-1}$, whereas all anti-ricin IgG-treated mice survived doses up to 125 ug/kg$^{-1}$. To evaluate protection from inhaled ricin toxin, groups of six CD1 mice were injected with 0 mg, 2.5 mg, or 5 mg of purified goat anti-ricin IgG (FIG. 8). Within 30 minutes, each group was exposed to 5 $LD_{50}$ of aerosolized ricin toxin. All the control (0 mg of antibody) animals died within 2 to 4 days after exposure to the toxin. Twenty percent of mice injected with 2.5 mg of anti-ricin IgG survived 14 days with mean time-to-death of 9 to 10 days. All mice injected with 5 mg of purified goat anti-ricin toxin IgG survived the challenge with aerosolized ricin toxin. Approximately 50-fold higher concentrations of heterologous antibody were required to protect against inhaled as compared to IV challenge.

Affinity-purified anti-ricin IgG was given to mice by small-particle aerosol. Each group of mice was challenged with a lethal dose of aerosolized ricin toxin 1 hour after antibody exposure. Survival data are summarized in Table 1. Fourteen of 16 mice pretreated with aerosolized anti-ricin IgG survived with minimal lung damage. The two non-survivors had obstructions due to proximal airway epithelial damage. In contrast, all 19 mice pretreated with inhaled non-specific IgG died of severe lung injury after exposure to aerosolized ricin toxin. These studies clearly demonstrate that localized anti-ricin antibody can protect the lung from injury caused by inhaled ricin toxin.

TABLE 1

Protection of Mice from Inhaled Ricin Toxin with Aerosolized Anti-Ricin IgG

| Group | Inhaled Antibody Dose | 14-Day Survival |
|---|---|---|
| Control-Non-Specific IgG | 54 µg/mouse | 0/19 |
| Anti-Ricin Toxin IgG | 24 µg/mouse | 8/8 |
| Anti-Ricin Toxin IgG | 82 µg/mouse | 6/8 |

EXAMPLE 4 cGMP Production of dgRTA

Inland Laboratories (Austin, Tex., catalogue no. 10153) produced and purified ricin deglycosylated A chain from chemically deglycosylated ricin D toxin under cGMP conditions as submitted to the FDA (BB-MS-2237, 0284-0400) and summarized here. Ricin toxin is extracted from the residual mash of the crushed castor bean, *Ricinus communis*, Euphorbiaceae. The toxin consists of two dissimilar polypeptide chains held together by a disulfide bond that joins cysteinyl residue near the carboxy terminus of the A-chain and the amino terminus of the B-chain. Deglycosylation of ricin was accomplished by treating the toxin with a mixture of sodium metaperiodate and sodium cyanoborohydride ar pH 3.5 for 1 hour at 4° C. (Thorpe et al., 1985, supra).

This procedure results in destruction of about 50% of the mannose and most fucose residues present in the RTA, whereas the N-acetylglucosamine and most of the xylose residues are unaffected (Vitetta & Thorpe, 1985, supra). Intact deglycosylated ricin is bound to an acid-treated sepharose 4B column and then split on the column into A and B chains with 2-mercaptoethanol. Deglycosylated A-chain is then eluted with 0.05M borate-NaCl buffer containing 2-mercaptoethanol. Subsequent to elution from the Sepharose 4B column, the dgRTA is dialyzed against 0.005M phosphate buffer (pH 6.5) with DTT and galactose. Any contaminating B chain is then removed by passing the A chain over CM-cellulose and Asialofetuin-Sepharose columns, which results in a highly purified dgRTA. For simplicity, this chemically modified product is called "deglycosylated ricin toxin A-chain (dgRTA).

The percentage of modified dgRTA that binds to ConA-Sepharose in 0.01 M lactose is a function of the amount of mannose destruction (Thorpe et al., 1985, supra). Further, chemically deglycosylated RTA that passed through ConA-Sepharose had a greatly reduced uptake into non-parenchymal cells.

Thus, chemically modified RTA that had a >90% non-retention on ConA-Sepharose was considered to have had about 50% of the mannose and most of the fucose destroyed by this procedure.

cGMP-produced dgRTA, 1.7 grams, (lot 9301) was dialyzed against PBS, pH 7.4, in accordance with cGMP standards. The dialyzed dgRTA solution was passed through a 0.22-µm filter and diluted with PBS to a protein content of 0.5±0.1 mg/ml.

The dialyzed dgRTA vaccine was lyophilized and vialed in accordance with cGMP standards. Dialyzed dgRTA vaccine was sterilized by filtration, and 0.2 ml of the product (100 µg) was dispensed into 6-ml clear vaccine vials. The filled vials were lyophilized, stoppered, capped, and labeled. A random sampling of vials was analyzed for moisture content, and the remainder of the vials was stored at −20° C. or 4° C. Each vial contains 100 µg of dgRTA vaccine.

Characterization of the dgRTA vaccine. In brief, SDS polyacrylamide gels demonstrate two peaks that represent variable carbohydrate content. Isoelectric focusing and HPLC demonstrated 95% to 99% purity. To further characterize the ricin dgRTA, chemical and biological assays were conducted. Results of N-terminal amino acid sequence and amino acid analysis were in agreement with-published data on RTA. Peptide mapping studies were completed on the dgRTA vaccine that will be used for future lot comparisons. The candidate dgRTA vaccine caused no primary dermal irritation in male and female rabbits. Serum from vaccinated mice exhibited ELISA antibody titers approximating 1:30,000 and toxin-neutralizing antibody titers ranged from 1:300 to 1:1,000. The product is stable for 2 years at −20° C. or 4° C. and for 3 months at room temperature.

EXAMPLE 5

Development of a Potency Assay

An in vivo biological potency assay for the candidate dgRTA vaccine was developed to measure lot-to-lot variation, changes in potency over time, and acceptable limits for use of the product. The assay involves a single intramuscular injection of varying concentrations of reconstituted dgRTA (1.25 to 20 ug) into groups of 10 BALB/c mice. At 3 weeks post-vaccination, the mice are challenged with an IP injection of 100 ug/kg or about seven IP-LD$_{50}$ of ricin toxin. The mice are observed and deaths scored for a 7-day post-challenge. The survival data on day 7 were used to calculate the mean effective dose (ED$_{50}$) and 95% confidence limits by probit analysis using SAS computer program with LOG$_{10}$ option or by Thompson and Weil (1947, Bact. Res 11, 115–145) moving average interpolation.

The potency of the pilot lot of vaccine was evaluated at the following stages of production: (1) on the cGMP-produced dgRTA before dialysis to remove the glycerol, (2) after dialysis against PBS, and (3) on the final vialed and lyophilized product. Table 2 summarizes the potency of the dgRTA vaccine at various stages of production. After dialysis, there was a small but not significant decrease in the potency of the vaccine. Vialing or lyophilization did not alter the potency of the dialyzed product.

The pilot lot of the lyophilized dgRTA vaccine was stored at −20° C. (−10° C. to −30° C.) and 4° C. (2° C. to 8° C.) for 3 years in a Quality Control Area At 3, 9, 12, 18, 24, 30, and 36 months of storage, vials of the vaccine stored at −20° C. were shipped to USAMRIID for analysis of the potency of the dgRTA vaccine. At 9, 12, 24, 30, and 36 months of storage, vials of vaccine stored at 4° C. were analyzed by this potency assay. A reference standard of cGMP-produced dgRTA (lot number 9301) was also analyzed at each time

TABLE 2

Potency of dgRTA Vaccine at Various Stages of Production

| Stage of Production | Observed ED$_{50}$ in µg/Mouse (95% Limit of Confidence) | Acceptance Criteria ED$_{50}$ in µg/Mouse | Pass (P) Fail (F) |
| --- | --- | --- | --- |
| Before Dialysis | 1.51 (0.63–2.28) | ≦10 | P |
| After Dialysis | 3.20 (1.75–4.77) | ≦10 | P |
| After Lyophilization | 2.34 (1.49–3.63) | ≦10 | P |

TABLE 3

Potency of dgRTA Vaccine Stored at −20° C. for 36 Months

| Months of Storage | Reference Lot 9301 ED50 in µg/Mouse 95% Confidence Limits | Test dgRTA | Acceptance Criteria | Pass (P) Fail (F) |
| --- | --- | --- | --- | --- |
| 3 | 1.51 (0.63–2.28) | 2.34 (1.49–3.63) | ≦10 | P |
| 9 | 1.25 (0.39–4.04) | 2.38 (1.97–2.87) | ≦10 | P |
| 12 | 1.74 (0.42–3.04) | 4.00 (2.58–6.00) | ≦10 | P |
| 18 | 2.70 (1.78–4.12) | 6.64 (4.82–9.10) | ≦10 | P |
| 24 | 5.40 (3.65–8.01) | 6.75 (4.61–9.54) | ≦10 | P |
| 30 | 2.50 (1.29–4.83) | 7.40 (4.82–12.35) | ≦10 | P |
| 36 | 2.50 (1.31–4.78) | 5.61 (3.10–10.18) | ≦10 | P | period for its potency. Tables 3 and 4 summarize the potency of the reference standard and the dgRTA vaccine when stored at −20° C. or 4° C., respectively, for 36 months. At both temperatures, the potency of the pilot lot of the candidate dgRTA vaccine tended to decrease (a higher ED$_{50}$) with time of storage; but at these time periods, the potency of the reference standard dgRTA also tended to decrease. However, the potency met the acceptance criterion of an $ED_{50}$, of <10 ug/mouse. This acceptance criterion was based on observation that mice immunized with three 10-ug doses of dgRTA vaccine that had a potency of 6.75 ug/mouse were completely protected from a challenge with aerosolized ricin toxin. Thus, the potency of this candidate vaccine appears to be relatively stable when stored at −20° C. or 4° C.

TABLE 4

Potency of dgRTA Vaccine Stored at 4° C. for 36 Months

| Months of Storage | Reference Lot 9301 $ED_{50}$ in µg/mouse (95% Confidence Limits) | Test dgRTA | Acceptance Criteria | Pass (P) Fail (F) |
|---|---|---|---|---|
| 9 | 1.25 (0.39–4.04) | 2.83 (0.08–9419) | ≤10 | P |
| 12 | 1.74 (0.42–3.04) | 4.27 (3.00–6.13) | ≤10 | P |
| 24 | 5.40 (3.65–8.01) | 10.00 (6.69–14.98) | ≤10 | P |
| 30 | 2.50 (1.29–4.83) | 7.06 (4.29–13.06) | ≤10 | P |
| 36 | 2.50 (1.31–4.78) | 5.00 (0.82–30.40) | ≤10 | P |

A portion of the pilot lot of the dgRTA vaccine that was held at −20° C. for 9 months was stored at room temperature (15° C. to 30° C.) over the course of 12 months. At 0, 2, and 4 weeks and at 3, 6, and 12 months, the integrity of dgRTA vaccine was determined by the potency assay for dgRTA.

Table 5 contains a summary of the data generated at each time point using this assay. Potency gradually decreased over the 12-month period; however, all $ED_{50}$ values remained within acceptable limits with the exception of the 6-month time period.

TABLE 5

Potency of dgRTA Vaccine Stored at Room Temperature (15° C. to 30° C.) for 12 Months

| Months of Storage | Reference Lot 9301 $ED_{50}$ in µg/Mouse (95% Confidence Limits) | Test dgRTA | Acceptance Criteria | Pass (P) Fail (F) |
|---|---|---|---|---|
| 0 | 1.51 (0.63–2.28) | 2.34 (1.49–3.63) | ≤10 | P |
| 0.5 | 1.17 (0.44–3.12) | 2.14 (1.47–3.12) | ≤10 | P |
| 1 | 3.54 (2.34–5.34) | 4.66 (3.56–6.11) | ≤10 | P |
| 3 | 1.74 (0.42–3.04) | 7.73 (5.40–11.34) | ≤10 | P |
| 6 | 2.64 (1.58–3.85) | 10.05 (7.31–14.22) | ≤10 | F |
| 12 | 2.70 (1.78–4.12) | 9.62 (7.00–12.74) | ≤10 | P |

Vials of the pilot lot of the candidate dgRTA vaccine that were stored at −20° C. for 9 months were reconstituted with 0.2 ml of bacteriostatic water and 0.8 ml of bacteriostatic saline (10 ug /0.1 ml). The reconstituted vaccine was stored in a refrigerator (2° C. to 8° C.) for 0 or 7 days and at room temperature (20° C. to 30° C.) for 0 or 24 hours. At the end of the storage period, the potency of the reconstituted dgRTA was determined by the in vivo potency assay. The results of this study are summarized in Table 6. The potency of the dgRTA vaccine tended to decrease under either storage condition, but the values were not statistically significant from the $ED_{50}$ of the control samples. Because of the poor fit of the data for probit analysis, it was recommended that this assay be repeated with additional time periods of storage. In a repeat study, vials of the pilot lot of the dgRTA vaccine that were stored at −20° C. for 22 months were reconstituted with 0.2 ml of bacteriostatic water and 0.3 ml of bacteriostatic saline (20 ug /0.1 ml.). The reconstituted vaccine was stored at 2° C. to 8° C. for 7 days or room temperature (15° C. to 30° C.) for 24 hours. At 0, 1, 4, 8, 24, 48, 96, and 168 hours in the refrigerator and 0, 1, 4, 8, and 24 hours at room temperature, the vials were examined for potency. Table 7 reflects the results of this study.

TABLE 6

Effect of Storage Conditions (Days) on the Potency of Reconstituted dgRTA Vaccine

| Days of Storage | Room Temperature (20° C. to 30° C.) $ED_{50}$ in µg/Mouse (95% | Refrigerated (2° C. to 8° C.) Confidence Limit) |
|---|---|---|
| 0.2 | 1.76 (0.73–4.25) | 1.25 (0.44–3.50) |
| 1 | 3.37 (2.12–5.35) | — |
| 7 | — | 4.35 (3.24–5.84) |

From these observations, it can be concluded that the reconstituted dgRTA vaccine retains its potency for 4 hours at room temperature or 24 hours in a refrigerator.

TABLE 7

Effect of Storage Conditions (Hours) on the Potency of Reconstituted dgRTA Vaccine

| Hours of Storage | Room Temperature (15° C. to 30° C.) $ED_{50}$ in µg/Mouse (95% | Refrigerated (2° C. to 8° C.) Confidence Limit)* |
|---|---|---|
| 0 | 6.63 (4.82–9.10) | 6.63 (4.82–9.10) |
| 1 | 5.12 (2.75–9.26) | 7.02 (4.69–11.86) |
| 4 | 4.04 (0.98–9.80) | 6.60 (3.71–13.15) |
| 8 | 8.27 (5.70–13.48) | 3.80 (2.44–5.58) |
| 24 | 5.72 (4.12–8.00) | 6.36 (4.38–9.19) |
| 48 | — | 11.41 (8.37–16.80) |
| 96 | | 7.10 (5.11–10.01) |
| 168 | | 7.88 (5.38–11.96) |

*23 minutes elapsed between reconstitution of dgRTA vaccine and injection of last dilution.

EXAMPLE 6

Stability of dgRTA Vaccine

Long-Term Stability Studies: The pilot lot of the candidate dgRTA vaccine was stored at <−15° C. or 2° C. to8° C. for 3 years in a Quality Control Area. At 0, 1, 3, 9, 12, 18, 24, 30, and 36 months of storage, vials of dgRTA vaccine stored at <−15° C. or 2° C. to 8° C. are to be reconstituted with 0.2 ml of water (50 ug/0.1 ml) and analyzed for physical-chemical characteristics, quantity, identity, sterility, endotoxin, and general safety. The 36-month data are pending. Analysis for samples of the dgRTA vaccine stored ≤−15° C. or 2° C. to 8° C. for 2 years show that except for the presence of very small particles in the pilot lot of vaccine stored at 2° C. to 8° C. for 2 years, all the other release tests met the acceptance s for the dgRTA vaccine. The presence of particles in the reconstituted vials was first observed at 12 months of storage at 2° C. to 8° C. (Table 8).

TABLE 8

Particulate Formation in Reconstituted dgRTA Vaccine Stored at ≤−15° C. to 2° C. to 8° C.

| | Presence of Particulates | |
|---|---|---|
| Months of Storage | Stored at 2° C. to 8° C. | Stored at ≤−15° C. |
| 0 | trace* | trace |
| 1 | trace | trace |
| 3 | trace | trace |
| 9 | trace | trace |
| 12 | Very Small Particles | trace |
| 18 | Very Small Particles | trace |
| 24 | Very Small Particles | trace |
| 30 | Very Small Particles | Very Small Particles |

*trace = barely discernible-practically particle free

In contrast, particulate formation was not observed in reconstituted vaccine until 30 month of storage at ≤−15° C. When the particulates were removed by centrifugation, all of the other tests were within acceptable specifications. Based on these results, the dgRTA vaccine maintained good stability for at least 30 month when stored at ≤−15° C. or 2° C. to 8° C.

Accelerated Stability Studies: A portion of the pilot lot of the vaccine was stored at 20° C. to 30° C. over the course of 12 months in a quality control area. At 1, 2, 3, 4, and 6 weeks and 2, 4, 6, 8, 10, and 12 months, the integrity of dgRTA vaccine was determined using a variety of release tests. The accelerated stability indicated that the lyophilized form of dgRTA vaccine was stable for all tests for a period of 2 weeks and was stable for all tests except particulate formation for 6 months. After 6 months, filtration to remove particulates resulted in a significant loss of protein and by 10 months, the purity of dgRTA vaccine, as measured by HPLC, started to decrease below specifications. Based on these results, the dgRTA vaccine retained good stability for 6 months at elevated temperatures.

Vials of the pilot lot of the candidate dgRTA vaccine that were stored at −20° C. were reconstituted with 0.2 ml of bacteriostatic water and stored at 2° C. to 8° C. for 7 days and 25° C. to 30° C. for 24 hours. At the end of the storage period, the integrity of the reconstituted dgRTA vaccine was determined using a variety of release tests.

The reconstituted dgRTA vaccine failed the visual assay for particulates, with noticeably large strands when stored at 15° C. to 30° C. for 24 hours and small size particles when stored at 2° C. to 8° C. for 7 days. When the particulates were removed by centrifugation, identity, purity, potency, and endotoxin levels were within acceptable specifications.

In a subsequent study at USAMRIID, vials of the pilot lot of the dgRTA vaccine that were stored at −20° C. were reconstituted with 0.2 ml of bacteriostatic water and 0.3 ml of bacteriostatic saline (20 ug/0.1 ml). The reconstituted vaccine was stored in a refrigerator (2° C. to 8° C.) for 7 days or at room temperature (15° C. to 30° C.) for 24 hours. At 0, 1, 4, 8, 24, 48, 96, and 128 hours storage in the refrigerator and 0, 1, 4, 8, and 24 hours at room temperature, the vials were examined for visual presence of particulates. The results of this study are summarized in Table 9. From these

TABLE 9

Effect of Storage on the Stability of Reconstituted dgRTA Vaccine

| | Presence of Particulates | |
|---|---|---|
| Hours of Storage | Room Temperature (15° C. to 30° C.) | Refrigerated (2° C. to 8° C.) |
| 0 | trace* | trace |
| 1 | trace | trace |
| 4 | trace | trace |
| 8 | trace | trace |
| 24 | Strands & Particulates | trace |
| 48 | — | Fine Particulates |
| 96 | — | Medium Particulates |
| 128 | — | Medium Particulates |

*trace = barely discernible-practically particle free observations, it can be concluded that the reconstituted dgRTA vaccine is stable for 8 hours at room temperature or 24 hours in a refrigerator before any visible particulates are observed in the product.

Figure 9A:
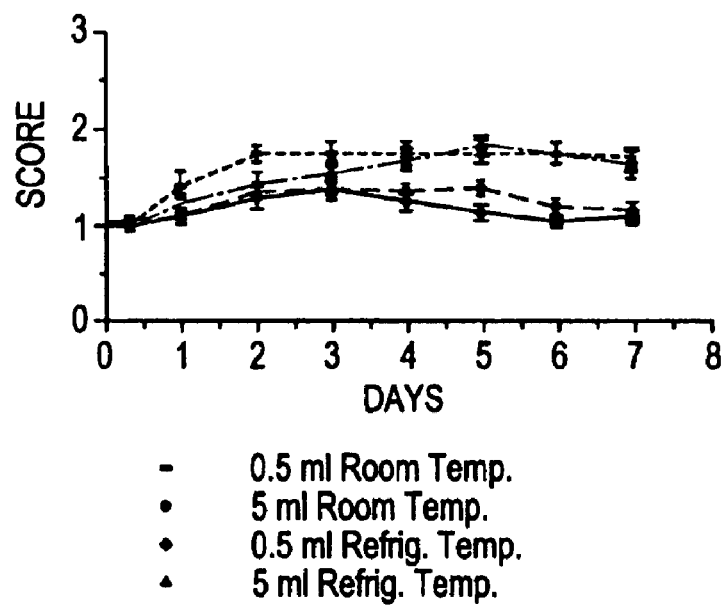
FIG. 9 A and B show effect of duration of storage at room temperature (15° C. to 30° C.) or refrigerator temperature (2° C. to 8° C.) on particulate formation (A) and clarity (B) of dgRTA vaccine reconstituted in 0.5 or 5 ml diluent.
Figure 9B:
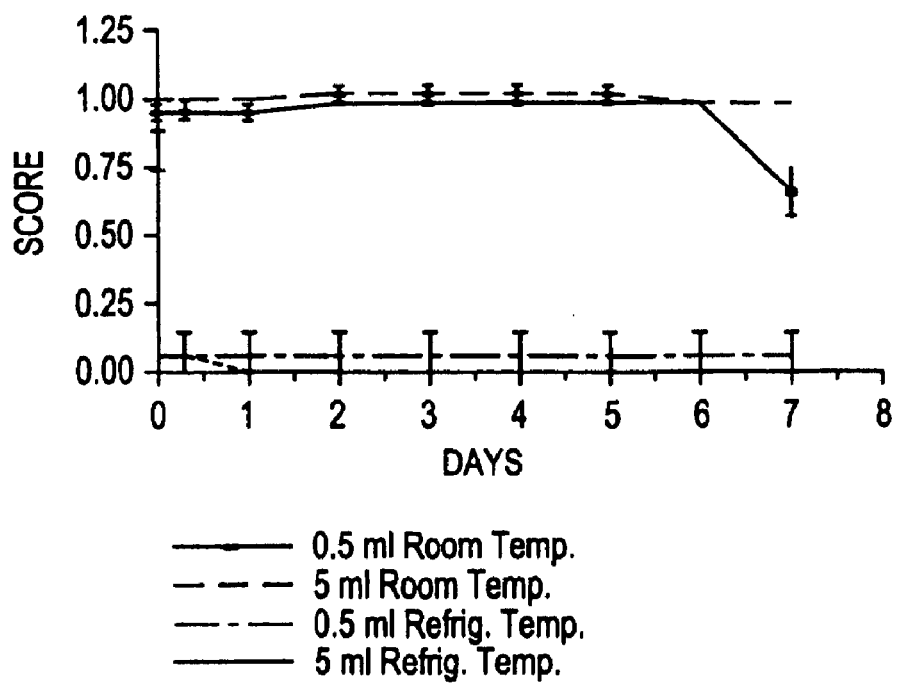

An attempt was made to quantify the effects of storage and temperature on rate of particulate formation and clarity in dgRTA vaccine that was reconstituted in 0.5 or 5 ml of diluent. The results are summarized in FIG. 9. This lot of dgRTA vaccine was stored at ≤−15° to −30° C. for 33 months. Particulates were formed immediately after the vaccine was reconstituted, with an average score of 1 on a scale of 0 to 10. The number of particulates increased to a maximal score of 1.4 to 1.8 on days 3 to 4 after the dgRTA was reconstituted. Dilution volume or storage temperature had little effect on particulate formation. Vials reconstituted with 0.5 ml of saline/water tended to be cloudy with a score of 1 on a scale of 0 to 10, whereas those reconstituted in 5 ml of saline were essentially clear. Additional studies are required to characterize the particles. Since the presence of particles does not alter the potency of the dgRTA vaccine, it is recommended that it be diluted with 5 ml of bacteriostatic saline and used within 6 to 8 hours of reconstitution.

EXAMPLE 7

Characterization of Particulates in Reconstituted dgRTA Vaccine

Figure 10:
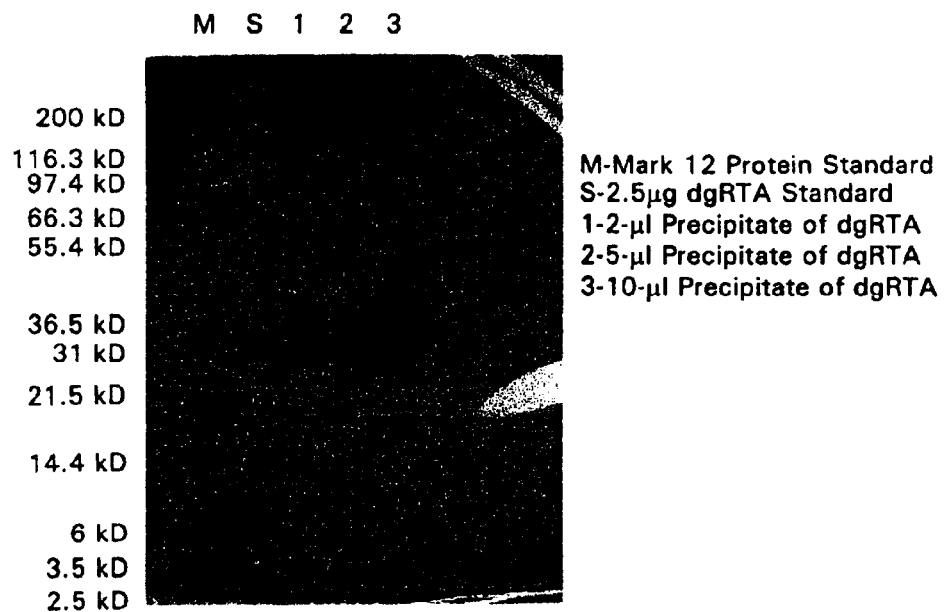
FIG. 10 shows SDS PAGE electrophoresis of particulates from reconstituted dgRTA vaccine.
Figure 11:
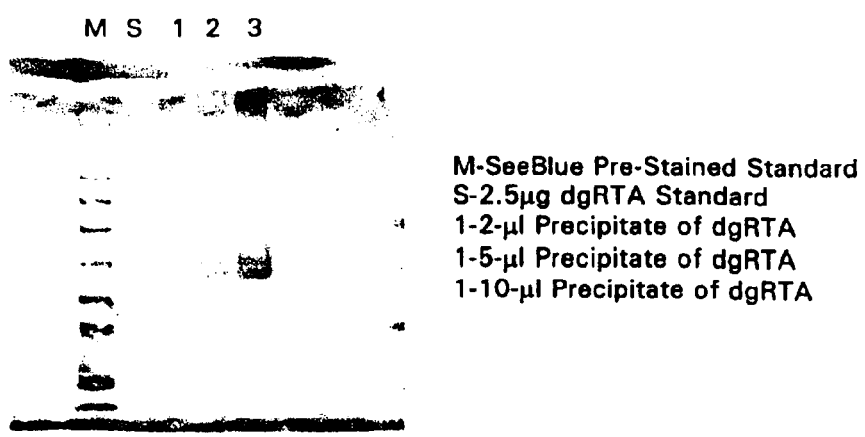
FIG. 11 shows western blot of particulates from reconstituted dgRTA vaccine.

Ten vials of dgRTA vaccine were reconstituted with 1 ml of bacteriostatic water. The contents of the vials were pooled and stored for 5 days at 4° C. Particulates in the reconstituted dgRTA vaccine were removed by centrifugation and the resulting Precipitate was washed twice with water. The washed precipitate was re-suspended in tribune sample buffer with 2 β mercaptoethanol and the solution was heated at 95° C. for 5 minutes. After heating, the proteins in the particulates were separated by SDS-PAGE and visualized by staining with Compass blue. The major proteins in the extract from the particulates in the reconstituted dgRTA vaccine had a molecular weight that was identical to the dgRTA standard (FIG. 10). In addition, there appeared to be aggregates at ~60 and 90 AD. This would suggest that the particulates in the reconstituted dgRTA vaccine are insoluble aggregates of the native protein. To confirm this, the extracts were analyzed by Western Blot that utilized an antibody specific for dgRTA. All of the proteins in the dgRTA standard and particulate extracts that were resolved on the SDS PAGE were also detected in the Western Blot (FIG. 11).

EXAMPLE 8

Safety of dgRTA Vaccine

To date there has been only one toxicological study on dgRTA (Soler-Rodriguez et al, 1993, *Exp. Cell. Res.* 206, 227–234). The $LD_{50}$ of dgRTA by IP or IV administration is 600 ug/25 g BALB/c mouse or 24 mg/kg. At IV doses of 120 to 420 ug/mouse, dgRTA resulted in early (24-hour) weight loss and late (10-day) accumulation as cites. In contrast, IP administration of 240 ug/mouse caused weight loss but not ascites. The mice maintained 80% of their body weight for several months after the single dose of dgRTA. An IV administration of 30 ug/mouse of dgRTA caused no loss in body weight. At higher doses of dgRTA, the weight loss was associated with reduced fluid and food intake. At day 10 or 11 following IP or IV administration of 240 ug/mouse of dgRTA, mice developed hypoalbuminemia, hyper-triglyceridemia, proteinuria, and glomerular damage.

Immunotoxins that contained tumor-reactive antibodies coupled to dgRTA and infused at 20 to 30 mg/kg in cancer patients caused VLS, myalgia, pulmonary edema, aphasia, kidney damage, and fever (Vitetta et al., 1993, supra). Because this toxicity occurred in patients treated with RTA immunotoxins of various specificities and with whole antibodies or Fab fragments linked two RTA, the immunotoxin's cell-targeting moiety is probably not responsible for inducing VLS (Vitetta et al , 1993, supra; Ghetie & Vitetta, 1994, *Curr. Opin. Immunol.* 6, 707–714). Mice, rats, guinea pigs, or cynomologous and rhesus monkeys do not exhibit VLS when treated with RTA-containing immunotoxins (Vitetta et al., 1993, supra; Ghetie & Vitetta, 1994, supra). In vitro models were developed to measure relevant consequences of endothelial cell damage over the 2 to 4 days in which RTA-immunotoxin-induced VLS occurs clinically (Soler-Rodriguez et al., 1993, supra; Lindstrom et al., 1997, supra). It was found that infusion of 1 to 2 ug/ml of RTA, dgRTA, recombinant RTA, or RTA immunotoxins significantly increased the permeability of human endothelial cell monolayers at time and concentrations consistent with onset of VLS in patients treated with dgRTA immunotoxins (Lindstrom et al., 1997, *Blood* 90, 2323–2334). These results have led to the conclusion that dgRTA contributes to VLS in treated patients. It is generally accepted that a serum concentration of 1 to 2 ug/ml (resulting from infusion of 20 to 30 mg) of dgRTA is predictive of severe VLS in patients treated with RTA immunotoxins (Vitetta et al., 1993, supra; Ohetie & Vitetta, 1994, *Curr Opin. Immunol* 6, 707–714; Lindstron et al., 1997, supra). Furthermore, dgRTA immunotoxins have a half-life ($t_{1/2}$) of 6 to 8 hours, which maintains a circulating concentration of 1 to 2 ug/ml of dgRTA for an extended period of time. In contrast, at a recommended dose of 10 ug of dgRTA vaccine injected intramuscularly in adult humans, it is physically impossible to obtain a circulating concentration of 1 to 2 ug/ml of dgRTA. In addition, the half-life of dgRTA is approximately 8 minutes. This would make it highly unlikely that vaccination of humans with 10-ug doses of dgRTA vaccine could cause VLS.

Figure 12A:
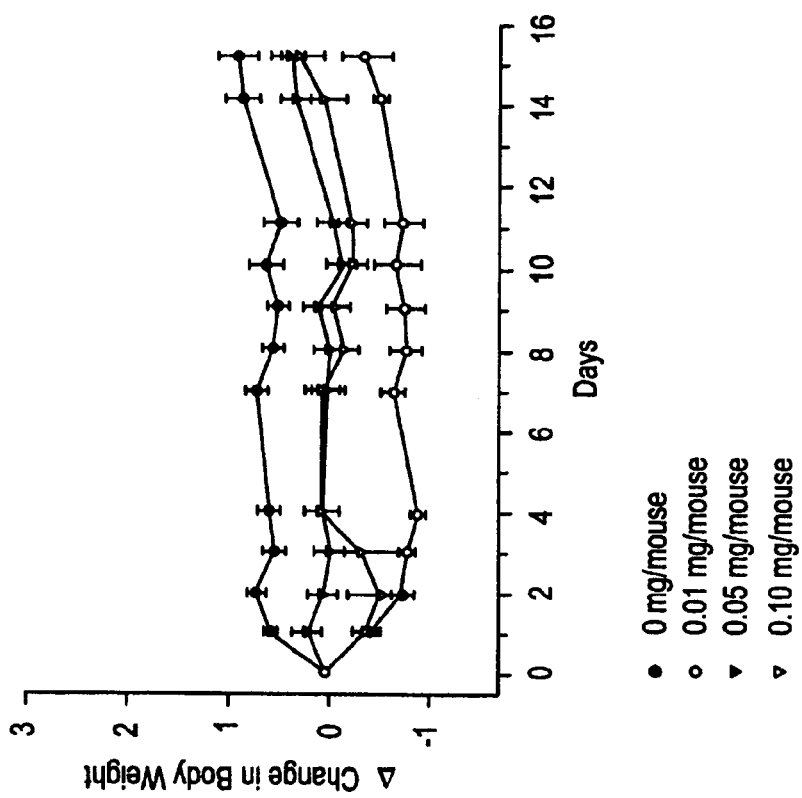
FIG. 12 A and B show body weight change of male and female BALB/c mice injected with acute doses of dgRTA vaccine or saline.
Figure 12B:
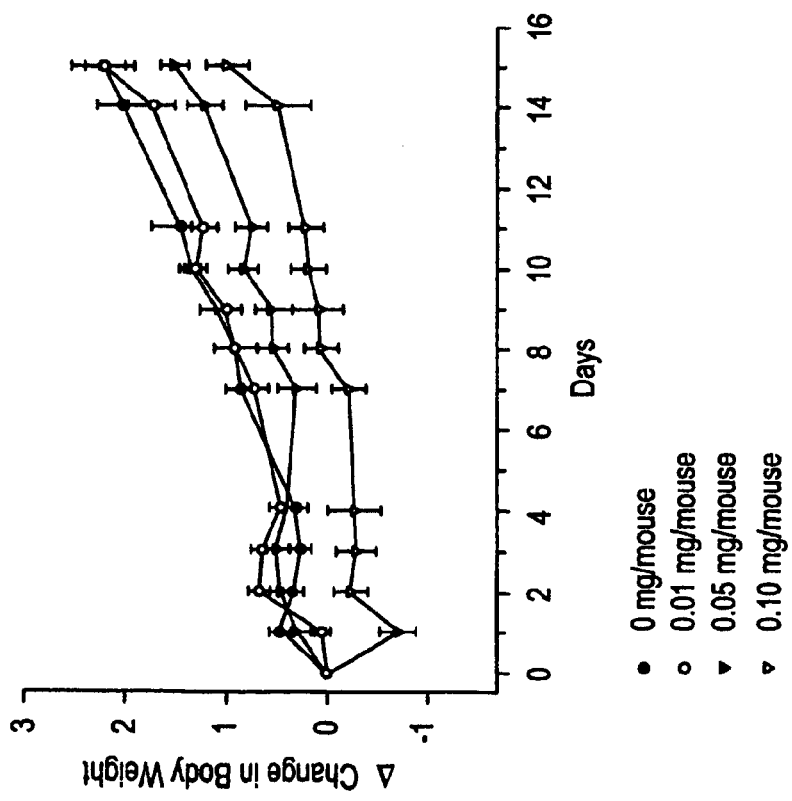

General safety testing involves IP injection of 0.5 ml of the reconstituted vaccine (10 ug) into each of at least two mice and 5 ml (100 ug) of the reconstituted vaccine into each of at least two guinea pigs. The safety test is successful if all of the nice and guinea pigs meet all the requirements: (1) they survive the 7-day test period; (2) they do not exhibit any response that is not specific for the vaccine; and (3) they weigh no less at the end of the test period than at the time of injection. Studies indicated that the dgRTA vaccine met general safety requirements. An acute safety study (Study Plan/Research Protocol-F97-09G) was conducted at USAMRIID in compliance with GLP regulations and is summarized in Table 10. Groups of 20 male and 20 female BALB/c mice were given a single IM injection of 0, 10, 50 or 100 ug of dgRTA vaccine. All mice survived for 15 days. However, as can be seen in FIG. 12, females were more susceptible to weight loss than males.

Males and females began to gain weight by day 8 and day 14, respectively. The loss of weight in female mice was not dose related in that animals that received 10 ug dgRTA lost weight, but animals that received 50 ug of dgRTA did not. This may indicate instability in weight (i.e., eating) for females that was more pronounced than for males. In a subsequent multi-dose study, female BALB/c mice that were dosed three times with 10 ug of dgRTA vaccine gained weight faster than saline controls over 147 days (see FIG. 14). The loss in body weight on day 1 was correlated with a reduction in food and water intake (Table 11). Similar dose-related responses were observed in both male and female mice

TABLE 10

Survival of Male and Female BALB/c Mice Injected with Acute Doses of dgRTA Vaccine

| Dose (μg/Mouse) | Sex | Dose (mg/kg) | Survived/Total Day 1 | Day 15 |
|---|---|---|---|---|
| 100 | Male | 4.37 ± 0.06 | 20/20 | 10/10 |
|  | Female | 5.23 ± 0.09 | 20/20 | 10/10 |
| 50 | Male | 2.25 ± 0.05 | 20/20 | 10/10 |
|  | Female | 2.58 ± 0.03 | 20/20 | 10/10 |
| 10 | Male | 0.44 ± 0.01 | 20/20 | 10/10 |
|  | Female | 0.51 ± 0.01 | 20/20 | 10/10 |
| 0 | Male | 0 | 20/20 | 10/10 |
|  | Female | 0 | 20/20 | 10/10 |

TABLE 11

Food and Water Intake in Male and Female BALB/c Mice on Day 1 after Dosing with the dgRTA Vaccine

| Dose (μg/Mouse) | Sex | Food Intake on Day 1 g/Mouse) | Water Intake on Day 1 g/Mouse) |
|---|---|---|---|
| 100 | Male | 2.1 | 1.8 |
|  | Female | 1.8 | 1.4 |
| 50 | Male | 2.4 | 2.7 |
|  | Female | 2.0 | 2.5 |
| 10 | Male | 2.8 | 2.8 |
|  | Female | 2.4 | 2.8 |
| 0 | Male | 3.0 | 2.9 |
|  | Female | 2.8 | 3.6 | injected with dgRTA vaccine. on days 1 and 15 post-injection, 10 male and 10 female mice were bled for the analysis of hematology and clinical chemistry parameters. Transient neutrophilia was the only significant observation (Table 12). These effects of dgRTA vaccine were dose related, and the 10-ug dose exhibited only a mild transient neutrophilia. At both time points, serum/plasma albumin concentrations in each dose group were in the normal range, which would indicate that VLS did not occur in mice given up to 100 ug of the vaccine.

After bleeding, necropsies were performed, and tissues were removed for histologic examination. There were no gross lesions attributable to the various doses of dgRTA vaccine. A single IM dose of the vaccine was associated with a dose-related local inflammatory response at the injection site. Inflammatory and degenerative changes at the site of injection were not resolved at 15 days post-injection. Morphologic evidence of systemic toxicity was limited to single cell necrosis in the intestinal crypt epithelium that had fully resolved by 15 days post-injection.

TABLE 12

Transient Neutrophilia in Male and Female BALB/c Mice Injected with Acute doses of dgRTA Vaccine

| Dose | | % Segmented Neutrophils | |
|---|---|---|---|
| (µg/Mouse) | Sex | Day 1 | Day 15 |
| 100 | Male | 62.3 ± 6.5 | 21.6 ± 6.6 |
|  | Female | 37.1 ± 10.9 | 17.7 ± 3.5 |
| 50 | Male | 52.7 ± 11.1 | 24.6 ± 8.9 |
|  | Female | 39.7 ± 7.6 | 20.7 ± 6.4 |
| 10 | Male | 39.8 ± 6.1 | 18.5 ± 4.6 |
|  | Female | 30.6 ± 12.0 | 15.9 ± 4.2 |
| 0 | Male | 21.7 ± 4.8 | 21.4 ± 5.9 |
|  | Female | 16.3 ± 3.7 | 18.4 ± 6.4 |

To quantify the dose response for the single cell necrosis (apoptosis) in the intestinal crypt epithelium, the following analysis was made on section of small intestine from the mice necropsied 1 day after injection with an acute dose of dgRTA vaccine: (1) Sections of small intestine from all male and female mice in each dose group were examined to quantify apoptosis; (2) total number of apoptotic cells within the crypts of an entire single transverse section of small intestine were counted; and (3) quantitative examination of blinded samples was performed independently by two board-certified veterinary pathologists. Table 13 summarizes the apoptosis in the small intestine of male and female mice 1-day after an acute dose of dgRTA vaccine.

TABLE 13

Group Summary of Small Intestinal Crypt Single Cell Necrosis (Apoptosis) in Mice Day 1 Post-Injection with dgRTA Vaccine

| Dose | Apoptotic Cell Count | |
|---|---|---|
| (µg/Mouse) | Male Mice | Female Mice |
| 100 | 566 ± 115* | 349 ± 82.6 |
| 50 | 464 ± 167 | 387 ± 150 |
| 10 | 186 ± 30.4 | 143 ± 56.8 |
| 0 | 24.4 ± 17.0 | 18.5 ± 7.3 |

*= Mean ± Standard Deviation of 20 Sections

Figure 13:
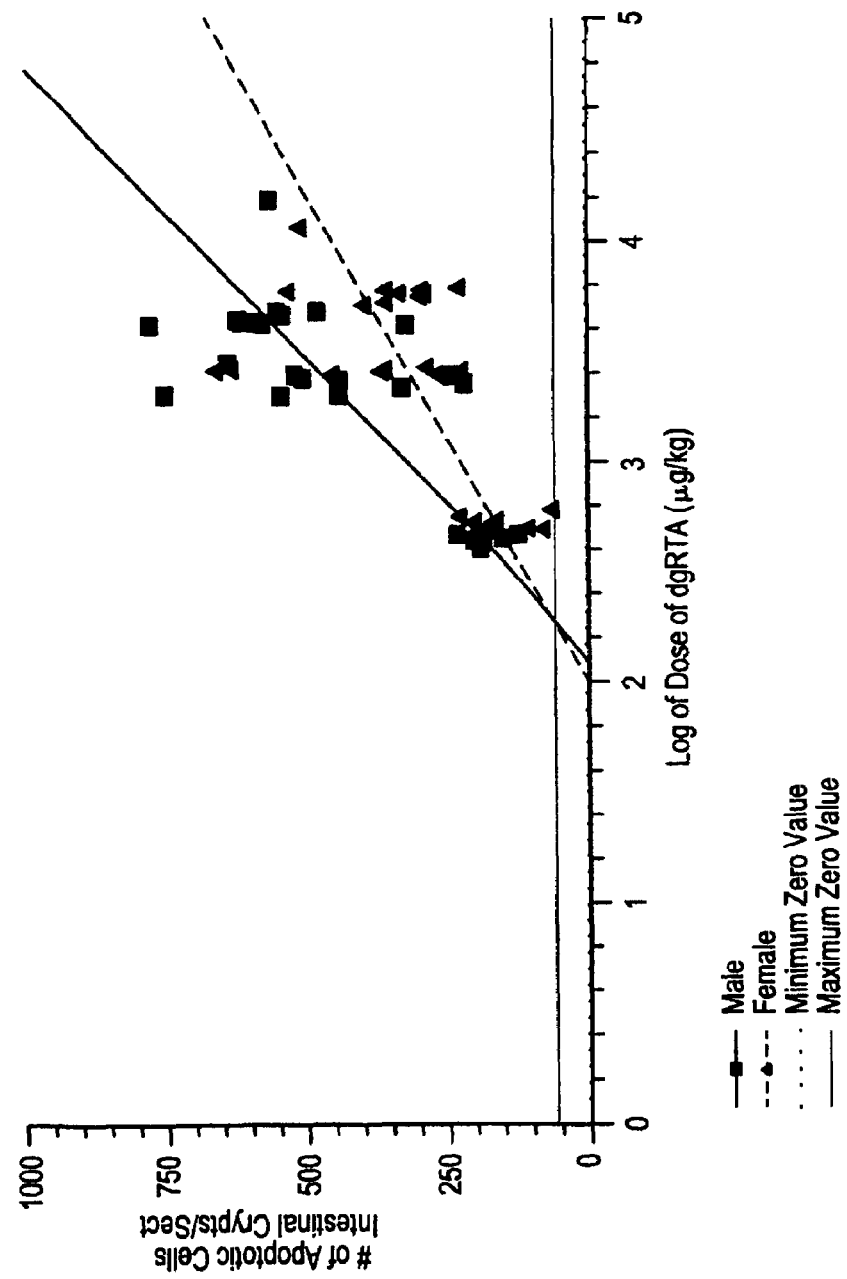
FIG. 13 shows a regression plot of dose-response in intestinal apoptosis on day 1 post-injection of dgRTA vaccine.

If the apoptotic count for the zero dose of dgRTA vaccine is considered the no-adverse-effect-level (NOAEL), then the regression analysis of the dose response to small intestine apoptosis can be used to calculate the NOAEL for dgRTA vaccine. FIG. 13 illustrates a linear regression plot of the data in Table 13 against the log dose of dgRTA (µg/kg). The correlation coefficients($r^2$) for the linear regression lines are 0.6612 and 0.4290, respectively, for the male and female mice. The slope is significantly different from zero for the male mice and female (p=<0.0001)). Within the limits of linearity of the regression lines, an estimated NOAEL can be calculated from standard curve of the line and the median, maximum, minimum zero dose values for small intestine apoptotic cell count (Table 14). In order to incorporate the variance of the zero dose,

TABLE 14

Estimated No-Observed-Adverse-Effect-Level (NOAEL) for dgRTA Vaccine from Linear Regression Analysis

| | Dose of dgRTA for NOAEL on Intestinal Apoptosis | |
|---|---|---|
| Sex | µg/Mouse Median (Minimum–Maximum) | µg/kg Median (Minimum–Maximum) |
| Male | 3.63 (3.35–4.63) | 159 (146–203) |
| Female | 2.41 (2.22–2.73) | 116 (107–132) | the data for the intestinal apoptosis in the non-zero dose mice was fitted to a quadratic regression, tested for extrapolation to the zero-dose, and the NOAEL determined by the minimum non-zero dose whose regression estimate is just significantly different at 5% confidence from the zero-dose group (using all zero-dose values). All regressions for the intestinal apoptotic cell counts of the non-zero dose groups were non-linear and extrapolated to the zero-dose. The NOAELs were well defined by these measurements (Table 15). The NOAEL values were slightly high from the quadratic regression analysis as compared to the linear regression analysis. Similar analyses were made on the dose response to percentage of segmented neutrophils on day 1 post-injection but the slopes of the linear regressions did not differ from zero and the data did not fit the quadratic regression model. Therefore, it was not possible to calculate a NOAEL for the dose response co percentage of segmented neutrophils.

TABLE 15

Estimated No-Observed-Adverse-Effect-Level (NOAEL) for dgRTA Vaccine from Quadratic Regression Analysis

| | Dose of dgRTA for NOAEL on Intestinal Apoptosis | |
|---|---|---|
| Sex | µg/Mouse | µg/kg |
| Male | 4.0 | 178 |
| Female | 6.2 | 316 |

At the proposed human dose of dgRTA vaccine, an individual would be injected with –0.15 ug/kg of dgRTA. The high-dose group of mice received between 4 and 5 mg/kg of dgRTA vaccine, which is 20 to 30 thousand times the chosen human dose. This high dose was not lethal but did cause toxicity as indicated by loss in body weight, decreased food and water intake, transient neutrophilia, local tissue reaction, and systemic transient increase in death of intestinal crypt cells. This dose-related toxicity was minimal in mice given the 10-ug dose of dgRTA vaccine The proposed human vaccinating dose of 0.15 ug/kg would be 25- to 1,000-fold less than the estimated NOAEL for dgRTA vaccine in mice.

EXAMPLE 9

Multiple-Dose Safety Studies on dgRTA Vaccine

A multiple-dose safety study (Study Plan/Research Protocol-F98-08G) was conducted in accordance with GLP standards. Three groups, each of which contained 570 female BALB/c mice, were given three IM injections (0, 27, and 55 days) of 10 us of dgRTA vaccine, human albumin, or bacteriostatic saline. On day 1 and on day 15 after the last injection, 20 mice from each group were necropsied. The remaining 530 mice in each treatment group were observed for 92 days after the last injection for mortality, morbidity, behavioral changes, and change in body weight. All of the mice injected with dgRTA vaccine survived for 147 days after the first dose of vaccine (Table 16).

TABLE 16

Summary of Mortality in Female Mice-GLP Study F98-08G

| Treatment (3 × 10 ug) | Number of Mice Alive at Start of Study | Number of Mice Alive on Day 147 of Study | % Mortality |
| --- | --- | --- | --- |
| dgRTA Vaccine | 530 | 530 | 0 |
| Human Albumin | 530 | 524 | 1.13 |
| Saline | 530 | 524 | 1.13 |

Twelve unscheduled deaths occurred during the study, but none were among the dgRTA vaccine-treated mice. The causes of death were within generally accepted historic norms for control BALB/c mice. They included the Saline Group: lymphosarcoma, 2 mice; round cell sarcoma, 1 mouse; myelogenous leukemia, 1 mouse; mammary adenocarcinoma, I mouse; euthanasia due to rectal prolapse, 1 mouse; and the Human Albumin Group: lymphosarcoma, 2 mice; round cell sarcoma, 1 mouse; malignant neoplasm, 1 mouse; not determined, 2 mice (1 malnourished, I excessive postmortem autolysis).

Of the 12 mice that died, 3 had symptoms of morbidity (1 tumor in the abdomen, 1 tumor in the neck, and 1 rectal prolapse) and had to be euthanized. The only behavioral changes were barbering of the nose and whiskers, head, neck and/or back of the mice. As summarized in Table 17, this behavior was observed in all three treatment groups with no significant difference by Fisher Exact Test.

TABLE 17

Summary of Barbering Behavior for Female Mice-GLP Study F98-08G

| Treatment | Total | Mice with Barbering Behavior | | Barbering of Nose & Whiskers | | Barbering of Head, Neck, and/or Back | |
| --- | --- | --- | --- | --- | --- | --- | --- |
| (3 × 10 ug) | # of Mice | # | % of Total | # | % of Total | # | % of Total |
| dgRTA Vaccine | 530 | 187 | 35.2 | 114 | 21.5 | 109 | 20.6 |

TABLE 17-continued

Summary of Barbering Behavior for Female Mice-GLP Study F98-08G

| Treatment | Total | Mice with Barbering Behavior | | Barbering of Nose & Whiskers | | Barbering of Head, Neck, and/or Back | |
| --- | --- | --- | --- | --- | --- | --- | --- |
| (3 × 10 ug) | # of Mice | # | % of Total | # | % of Total | # | % of Total |
| Human Albumin | 524 | 344 | 65.6 | 228 | 43.5 | 193 | 36.8 |
| Saline | 524 | 257 | 49.0 | 234 | 44.7 | 111 | 21.2 |

Figure 14:
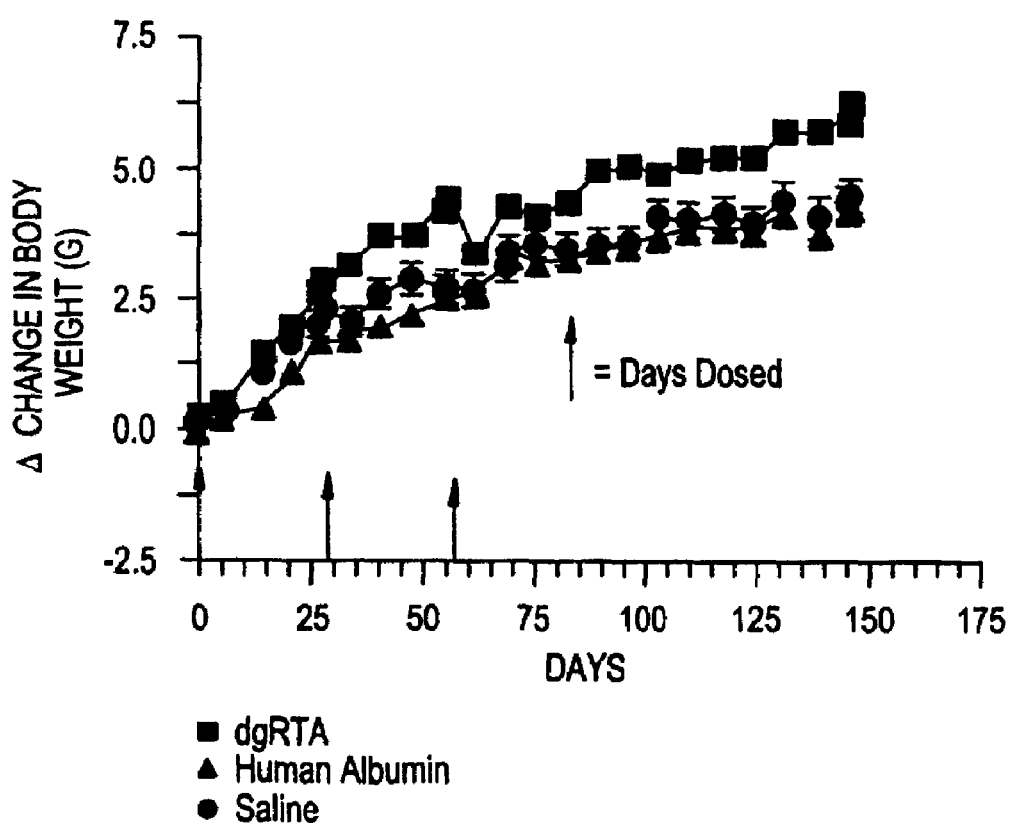
FIG. 14 body weight change of female BALB/c mice injected with multiple doses of dgRTA vaccine, human albumin, or saline.

For all three treatment groups, mice gained body weight for the 147 days of the study. A repeat measures analysis of variance (ANOVA) on change in body weight from baseline was performed. There was a significant difference in linear growth between dgRTA vaccine and human albumin ($p=0.0065$) or saline ($p=0.0001$) treatment groups (FIG. 14). A higher growth rate was seen in the dgRTA vaccine group than in the control groups. No indications of toxicity, as manifested by weight loss or decreased gain in body weight, were observed in mice given the dgRTA vaccine.

On days 1, 15, and 92 after the last vaccine injection, 20 mice in each treatment group were bled for hematology and clinical chemistry. Mean values for all tests from the mice injected with dgRTA vaccine were in the normal range for this species, but outliers were observed in all treatment groups Transient neutrophilia was not observed in mice injected with dgRTA vaccine. At all time periods, serum/plasma albumin concentrations in mice injected with multiple doses of 10 ug of dgRTA vaccine were in the normal range.

Overall tests by ANOVA indicated significant (overall p value (0.05) treatment differences at days 1, 15, and 92 after the last injection. As can be seen in Table 18, the only consistent treatment difference was a significant elevation in serum/plasma IgG in the dgRTA vaccine-injected mice as compared to controls given human albumin or saline. These results indicate that dgRTA stimulates production of total IgG.

TABLE 18

Serum Total IgG in Female BALB/c Mice at Various Times after the Last Dosing

| Treatment | Day 1 | Day 15 | Day 92 |
| --- | --- | --- | --- |
| | mg/dl of Total IgG | | |
| dgRTA Vaccine | 564 ± 74* | 667 ± 39 | 779 ± 42 |
| Human Albumin | 229 ± 14 | 261 ± 22 | 483 ± 54 |
| Saline | 213 ± 18 | 210 ± 28 | 360 ± 30 |

*= Standard Error of the Mean

After being bled, 20 mice per treatment group were euthanized and necropsied on days 1, 15, and 92 following the three IM injections of dgRTA vaccine, human albumin, or saline. There were no gross lesions that could be attributed to the different treatments. A full complement of tissues from five mice per group was examined histologically for each time point. The IM administration of dgRTA was associated with a local inflammatory reaction at the injection site that gradually resolved to negligible levels over the study period. In contrast to the single dose toxicity study, there was an insignificant increase in death of intestinal crypt epithelial cells in the dgRTA vaccine-treated group. No other local or systemic pathologic findings were attributable to the different treatments.

Mild to moderate dermatitis and panniculitis, moderate myositis, and mild myofiber necrosis and hemorrhage were present at the injection sites of dgRTA vaccine-treated mice that were necropsied on day 1 after the last injection. Minimal to no inflammatory changes were observed at injection sites of saline-treated control mice. The reaction to albumin was intermediate to that induced by saline and dgRTA vaccine The dgRTA vaccine-induced inflammatory changes were diminished by day 15 post-injection. Moderate myofiber regeneration was also apparent at the site of injection of dgRTA vaccine-treated mice on day 15. Histopathologic changes at dgRTA vaccine injection sites continued to resolve. They were limited to minimal panniculitis and minimal myositis in 2/5 mice and minimal myositis without panniculitis in 1/5 mice at day 92 post-injection. No histopathologic changes were noted at the injection sites of saline- or albumin-treated mice at day 92 post-injection.

Minimal local tissue reaction would be expected to occur with the proposed human immunization schedule for dgRTA vaccine. At the proposed human dose of dgRTA vaccine, three immunizations in mice resulted in some local reaction at the site of the IM injection. This reaction resolved completely by day 92 with no apparent muscle damage. It should be noted that the concentration was fivefold higher in the volume (0.1 ml). That was given to mice than what will be given to humans in a 0.5 ml volume. No other toxic effects were associated with the 10-ug dose of this vaccine.

EXAMPLE 10

Efficacy Studies with dgRTA Vaccine

Rats and mice were exposed to lethal aerosol concentrations of ricin within a Class II biological safety cabinet. The aerosols were generated using a three-jet Collison nebulizer that contained 10 ml of the toxin at the required dilution in sterile PBS. The nebulizer, driven by compressed air, produced an aerosol at a flow rate of 7.5 l/min and a mass median aerosol diameter of 1.2 um. The aerosol was mixed with 4.5 l/min of secondary air for a total system flow rate of 12 l/min. Aerosol sampling was performed with all glass impingers (AGI) that contained a 6 l/min critical orifice to regulate flow. The toxin was impinged in 10 ml of sterile PBS in the AGI. Aerosols were sampled continuously during each exposure trial. The protein concentration in the AGI was determined using the Micro-BCA protein assay. Aerosol concentrations were calculated and the inhaled doses were estimated using Guyton's formula for minute volume calculations of the rodents.

EXAMPLE 11

Efficacy of Two and Three Doses in Rats and Mice

A two- and three-dose vaccine efficacy study was performed in male and female BALB/c mice and Fischer rats Six groups, consisting of 20 males and 20 females each for both mice and rats, were vaccinated at 0 and 4 or 0, 4, and 8 weeks by IM injection containing either 10 ug of the dgRTA vaccine or saline. At 90 days after the last vaccination, mice and rats were exposed to whole body dynamic aerosols of either five $LD_{50}$) of ricin toxin D or saline in the groups:

3SR-Three doses of saline and ricin toxin challenge (control)
2AR-Two doses of dgRTA vaccine and ricin toxin challenge
3AR-Three doses of dgRTA vaccine and ricin toxin challenge
2AS-Two doses of dgRTA vaccine and saline challenge
3AS-Three doses of dgRTA vaccine and saline challenge
3SS-Three doses of saline and saline challenge Survival and mean time to death are presented in Table 19. All of the mice and 95% of the rats vaccinated with two or three doses of dgRTA vaccine survived the aerosol challenge with ricin toxin, whereas all saline-injected and toxin-challenged animals died. No significant effects of sex, species, or number of vaccine doses (two vs. three) were observed on survival of animals vaccinated with dgRTA vaccine and challenged with ricin toxin.

TABLE 19

Survival and Mean Time to Death for 14 days after Aerosol Challenge with Ricin Toxin D or Saline

| | | Mouse | | Rat | |
|---|---|---|---|---|---|
| Group | Sex | Survival/Total | Mean Time to Death | Survival/Total | Mean Time to Death |
| 3SR | Male | 0/10 | 3.8 days | 0/10 | 2.3 days |
| | Female | 0/10 | 4.2 days | 0/10 | 1.8 days |
| 2AR | Male | 10/10 | NA | 10/10 | NA |
| | Female | 10/10 | NA | 10/10 | NA |
| 3AR | Male | 10/10 | NA | 9/10 | 10 days |
| | Female | 10/10 | NA | 10/10 | NA |
| 2AS | Male | 10/10 | NA | 10/10 | NA |
| | Female | 10/10 | NA | 10/10 | NA |
| 3AS | Male | 10/10 | NA | 10/10 | NA |
| | Female | 10/10 | NA | 10/10 | NA |
| 3SS | Male | 10/10 | NA | 10/10 | NA |
| | Female | 10/10 | NA | 10/10 | NA |

NA = Not Applicable

Figure 15A:
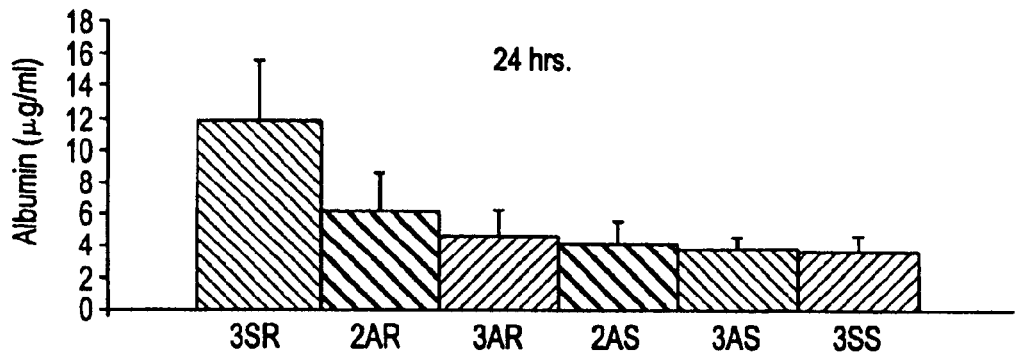
FIGS. 15 A and B show mouse BAL fluid post-ricin toxin aerosol challenge.
Figure 15B:
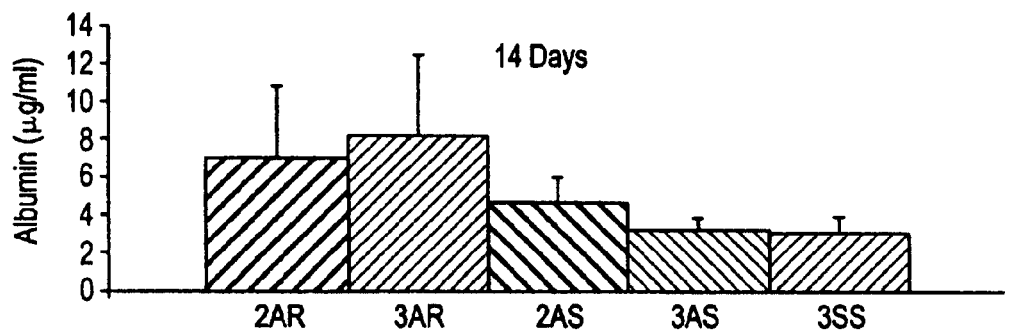
Figure 16A:
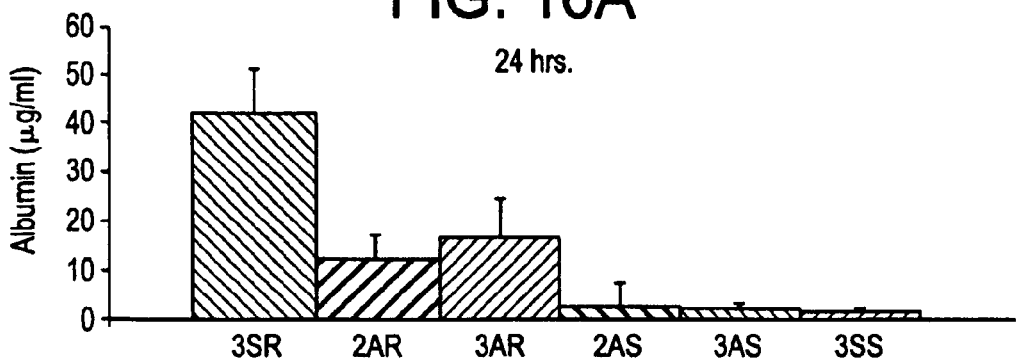
FIG. 16 A and B show rat BAL fluid post-ricin aerosol challenge.
Figure 16B:
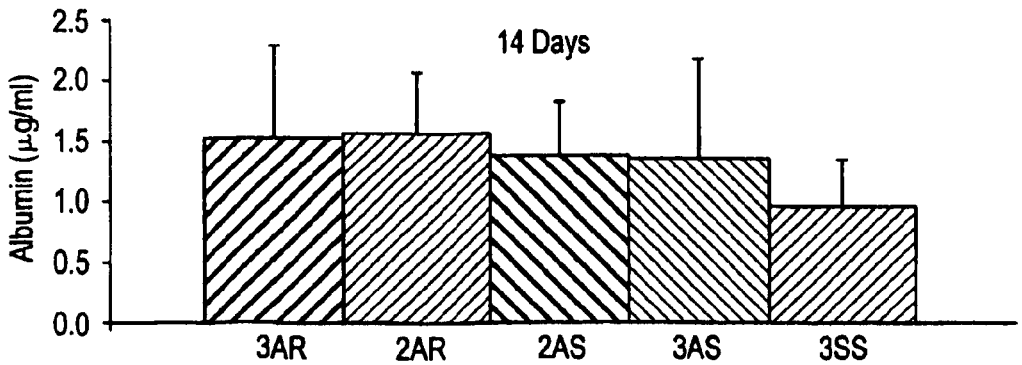

On days 1 and 14 following challenge with ricin toxin or saline, BAL procedures were performed on 10 surviving mice and rats in each treatment group. The BAL fluid was analyzed for albumin concentration. The data are summarized in FIGS. 15 and 16.

In both mice and rats, saline injection and ricin toxin challenge resulted in a marked increase in the albumin concentration of the BAL fluid on day 1 after exposure. As noted earlier, an elevation in the albumin concentration in the BAL fluid is a biochemical marker of lung injury. Vaccination with one or two doses of the dgRTA vaccine prevented or significantly reduced the ricin toxin-stimulated elevation in albumin content of BAL fluid. By day 14, ricin-challenged controls had died. In the animals vaccinated with dgRTA vaccine, the albumin content of the BAL fluid had returned to pre-exposure concentrations. No significant effects of sex, species, or number of doses (two vs. three) were observed for the protection from lung injury in animals vaccinated with dgRTA vaccine and challenged with ricin toxin. It can be concluded from these results that vaccination with the dgRTA vaccine not only prevented the lethal effect of aerosolized ricin toxin but also reduced lung injury.

After completion of the BAL procedure on days 1 and 14, lungs were removed and saved for histologic examination. The following is a summary of the histopathologic lesions observed in the lungs of mice and rats vaccinated with two or three doses of dgRTA vaccine before exposure to aerosolized ricin toxin. On day 1 after challenge, the lungs of control mice and rats treated with saline had perivascular edema, alveolar flooding, acute peribronchovasculitis, acute bronchitis, acute alveolitis, perivascular cuffing, and eosinophilia In rats and mice vaccinated with dgRTA vaccine, alveolar flooding was either reduced or absent. By day 14, all ricin-challenged controls had died. In animals vaccinated with dgRTA vaccine, pulmonary lesions consisted of goblet cell metaplasia, subacute peribronchovasculitis, subacute mucinous bronchitis, subacute alveolitis, alveolar histiocytosis, fibroplasia, perivascular cuffing, and eosinophilia that appeared to be resolving. While vaccination with dgRTA vaccine did prevent alveolar flooding, which is probably the major cause of lethality by aerosolized ricin toxin, it did not eliminate the lung injury that was associated with aerosol exposure to this toxin. No significant effects of sex, rodent species, or number of doses (two vs. Three) were observed in the reduction of lung injury in animals vaccinated with dgRTA vaccine and challenged with ricin toxin Eosinophilia was found to be a transient phenomenon in vaccinated mice and rats challenged with aerosolized ricin. Eosinophilia did not occur in the absence of ricin challenge. These findings are consistent with those of other investigators, including Thorpe et al. (1989, supra) and Underwood et al. (1995, *Immunology* 85, 256–261).

Long Term Efficacy studies with dgRTA vaccine

Mice injected with three doses of dgRTA vaccine, human albumin, or saline as part of the multiple-dose safety study (Study Plan/Research Protocol-F98-08G) were also used for a long-term efficacy study. At 3, 6, 9, 12, and 18 months following the last injection, 20 female mice in each treatment group were challenged by exposure to a whole-body dynamic aerosol containing five $LD_{50}$ of ricin toxin D. Survival of the animals challenged at 3, 6, 9, 12, and 18 months is shown in Table 20. All mice immunized with the dgRTA vaccine survived exposure to aerosolized ricin at 3, 6, 9, and 12 months after the last injection, whereas all human albumin and saline-treated control animals died. At 18 months after the last vaccination, 95% of the mice immunized with dgRTA survived exposure to aerosolized ricin toxin whereas all the controls died. Since approximately 20% of the mice that were on the study for 18 to 21 months died of age-related illness, it is possible that the ricin toxin did not cause the one early death in the dgRTA vaccine group.

TABLE 20

Survival and Mean Time to Death after Aerosol Challenge with Ricin Toxin D at 3, 6, 9, 12, and 18 Months

| Months after Last Injection | dgRTA Vaccine | | Human Albumin | | Saline | |
|---|---|---|---|---|---|---|
| | Survival/Total | Mean Time to Death (d) | Survival/Total | Mean Time to Death (d) | Survival/Total | Mean Time to Death (d) |
| 3 | 20/20 | NA | 0/20 | 4.0 | 0/20 | 3.7 |
| 6 | 20/20 | NA | 0/20 | 4.1 | 0/20 | 4.0 |
| 9 | 20/20 | NA | 0/20 | 4.1 | 0/20 | 4.0 |
| 12 | 20/20 | NA | 0/20 | 4.0 | 0/20 | 4.1 |
| 18 | 19/20 | 3 | 0/20 | 4.0 | 0/20 | 3.8 |

(d) = Days
NA = Not Applicable

EXAMPLE 12

Duration of Lung Injury in Surviving Mice Vaccinated with dgRTA Vaccine and Challenged with Aerosolized Ricin Toxin D Five dgRTA vaccinated mice that survived challenge with aerosolized ricin toxin at 3 months after the last vaccination were euthanized and necropsied on days 14, 28, 56, and 112 post-challenge The lungs were examined histologically to determine the long-term sequelae of ricin toxin challenge in mice vaccinated with dgRTA vaccine. Lungs from mice euthanized on days 14, 28, 56, and 112 post-challenge have been examined for long-term sequelae. Changes attributable to ricin challenge gradually resolved at each subsequent examination time point. There was moderate infiltration of the perivascular interstitium by lymphocytes, eosinophils, plasma cells, and macrophages (perivascular); moderate goblet cell metaplasia of bronchiolar epithelium; minimal to mild infiltration of alveoli by inflammatory cells (alveolitis); and minimal alveolar histiocytosis in 5/5 mice at day 14 post-challenge. One mouse also exhibited mild bronchiolar-alveolar fibroplasia at day 14. The incidence of histopathologic changes was reduced in number and severity, and eosinophilia 1 sad resolved by day 28. By day 56, perivasculitis and goblet cell metaplasia were generally minimal, and mild alveolitis and minimal alveolar histiocytosis were present in only one mouse. Fibroplasia was not observed. At day 112, findings were limited to minimal perivasculitis.

EXAMPLE 13

Immunological Studies with dgRTA Vaccine

Figure 17:
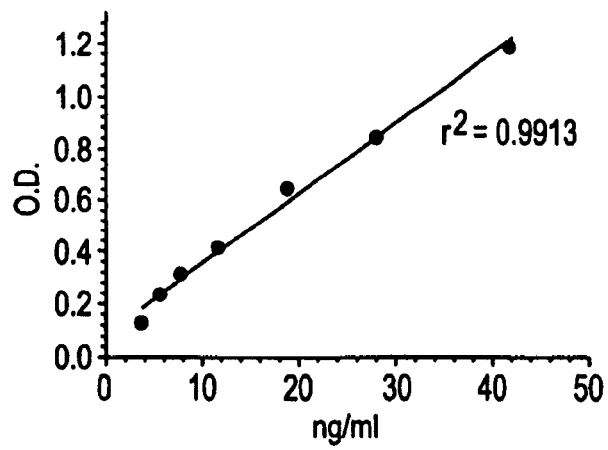
FIG. 17 shows a standard curve for mouse anti-ricin toxin IgG.

An ELISA and an in vitro toxin neutralization assay were developed to measure, respectively serum/plasma total and neutralizing anti-ricin IgG antibodies. Initially, a direct anti-ricin toxin IgG ELISA was developed in which the reciprocal titer was determined as the highest dilution that gave an optical density of two standard deviations above background (Hewetson et al., 1995, *Vaccine Res.* 4, 179–187). Recently, this assay was modified to quantitate the anti-ricin concentration by interpolating the highest dilution that falls on a standard curve. This standard curve (FIG. 17) was constructed using Protein A purified IgG from mice vaccinated with dgRTA vaccine The ricin neutralization assay was developed to measure the ability of serum/plasma anti-ricin antibodies to protect EL-4 and vero cells from the cytotoxic effects of ricin toxin D. Reciprocal titers were determined as the highest dilution of sera that protects at least 10% of the cells from the cytotoxic effects of ricin toxin D.

Figure 18:
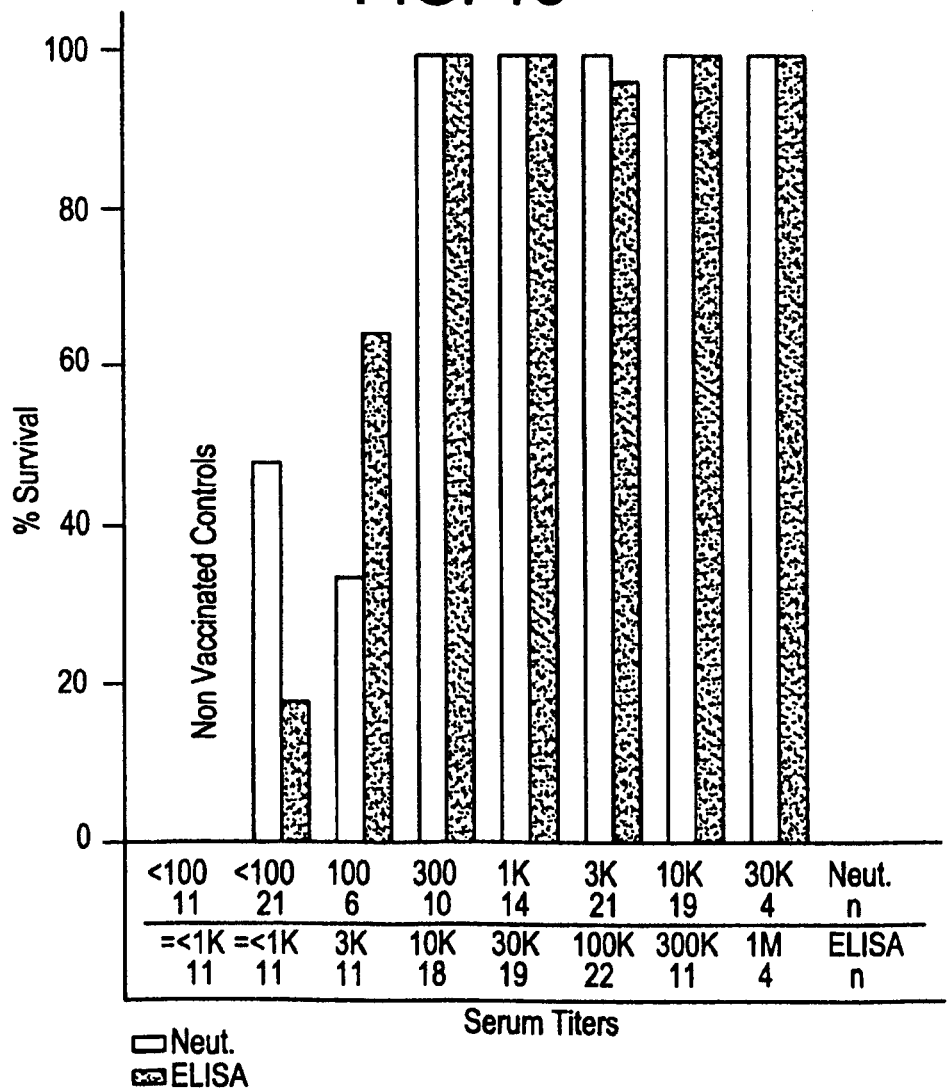
FIG. 18 shows a comparison of immune response to survival in mice vaccinated with dgRTA vaccine and exposed to aerosolized ricin toxin D.

From data on dose escalation studies with pre-GMP lots of dgRTA vaccine, survival of individual mice after challenge with aerosolized ricin toxin was compared to their pre-exposure antibody responses to vaccination with dgRTA vaccine (FIG. 18). Mice that had an anti-ricin toxin ELISA titer >10,000 and a neutralizing antibody titer >300 survived a challenge with lethal exposure to aerosolized ricin toxin D.

When rats or mice were vaccinated with dgRTA vaccine, the ELISA and neutralization titers always correlated with survival results. However, when pre-GMP lots of dgRTA vaccine were treated with organic solvents during encapsulation into microspheres, higher anti-ricin toxin titers were observed, but neutralizing antibodies were not detected and mice did not survive aerosol challenge with ricin toxin (Table 21). This indicates that alterations in the structure/conformation of the dgRTA molecule can result in production of antibodies that bind ricin toxin but do not neutralize lethal effects by aerosol exposure.

TABLE 21

Antibody Response and Survival after Exposure to Five LD$_{50}$ of Aerosolized Ricin in Mice Vaccinatad with Either dgRTA Vaccine or Encapsulated dgRTA

| Treatment | ELISA Titers | | Neutralization Titers | | Survived/Total |
|---|---|---|---|---|---|
| | GMT[a] | Range | GMT | Range | |
| dgRTA Vaccine | 53,000 | 5,100–163,000 | 117 | 100–400 | 9/10 |
| Encapsulated dgRTA | 102,000 | 5,122–163,000 | 0 | 0 | 0/10 |

[a]Geometric mean (antibody) titer

EXAMPLE 14

Antibody Responses in Mice and Rats Vaccinated with Two or Three Doses of dgRTA Vaccine Six groups of mice and rats, consisting of 10 males and 10 females each, were vaccinated at 0 and 4 or 0, 4, and 8 weeks by IM injection containing 10 ug of dgRTA vaccine or saline. At 90 days after the last vaccination, mice and rats were exposed to whole body dynamic aerosols of either five LD$_{50}$ of ricin toxin D or saline. One week before exposure, blood samples were obtained from the periorbital venous sinus of mice and the orbital venous plexus of rats. The blood samples were analyzed for anti-ricin toxin IgG by ELISA and for toxin-neutralizing antibodies by the in vitro assay. The antibody responses in mice and rats to two or three TM doses of dgRTA vaccine are shown in Table 22. At two or three doses, mice had mean total IgG anti-ricin toxin ELISA titers of 194K to 300K and anti-ricin neutralizing antibody titers of 1,700 to 2,200. Rats exhibited lower antibody titers by both tests. These titers correlated with high survival rates when -vaccinated mice and rats were exposed to 5 LD$_{50}$ of aerosolized ricin toxin (Tables 19 and 21). Similar antibody responses were observed in vaccinated male and female mice and rats . Therefore, data from both sexes were used to calculate the antibody response presented in Table 22 Mice had 4- to 5-fold higher anti-ricin toxin-neutralizing antibody titers than did rats.

TABLE 22

Antibody Response in Mice and Rats Vaccinated with Two or Three Doses of dgRTA Vaccine

| Treatment Group | Mouse Serum Anti-Ricin IgG | | Rat Serum Anti-Ricin IgG | |
|---|---|---|---|---|
| | ELISA GMT (1:xK) | Neutralizing GMT (1:x) | ELISA GMT (1:xK) | Neutralizing GMT (1:x) |
| Two Vaccinations with dgRTA | 194 (160–237) | 1723 (1366–2174) | 5.31 (4.22–6.69) | 308 (258–368) |
| Three Vaccinations with dgRTA | 300 (250–359) | 2192 (1901–2529) | 6.95 (5.32–9.09) | 274 (235–321) |
| Vehicle (Saline) | 0 | 0 | 0 | 0 |

EXAMPLE 15

Immune Responses of Mice in the Long-Term Efficacy Study with dgRTA Vaccine

Mice injected with three doses of dgRTA vaccine, human albumin, or saline as part of the multiple-dose safety study (Study Plan/Research Protocol F98-08G) were also used for the long-term efficacy study. At 1, 15, and 92 days and at 3, 6, 9, 12, and 18 months after the last injection, blood samples were obtained from the periorbital venous sinus of 20 mice. These blood samples are to be analyzed for anti-ricin IgG antibodies by the quantitative ELISA and neutralizing antibodies by the in vitro assay. This is an ongoing study. Blood was collected up to 18 months post-vaccination and corresponding serum samples through 18 months after the last injection have been analyzed for total IgG anti-ricin content and the results are summarized in Table 23.

TABLE 23

Immune Response and Survival after Aerosol Challenge with Ricin Toxin of Mice at Various Times after the Last Dose of dgRTA Vaccine

| Time after Last Dose of dgRTA Vaccine | Quantitative ELISA dgRTA Vaccine | | Survival |
|---|---|---|---|
| | Anti-Ricin[1,2] IgG (mg/ml) | Dilution | Survived/Total |
| 1 Day[3] | 3.15 ± 0.42[5] | 116,000 ± 17,900 | Not Challenged |
| 15 Days[3] | 4.32 ± 0.46 | 176,000 ± 16,200 | Not Challenged |
| 3 Months[3] | 3.87 ± 0.27 | 197,000 ± 7,880 | Not Challenged |
| 3 Months[4] | 3.92 ± 0.44 | 170,000 ± 16,200 | 20/20 |
| 6 Months[4] | 4.34 ± 0.34 | 189,000 ± 11,100 | 20/20 |
| 9 Months[4] | 2.81 ± 0.52 | 81,920 ± 14,095 | 20/20 |
| 12 Months[4] | 1.39 ± 0.14 | 71,120 ± 10448 | 20/20 |
| 18 Months[4] | 1.68 ± 0.28 | 89,600 ± 17619 | 19/20 |

[1]No anti-ricin IgG was detected in the serum of mice injected with human albumin or saline.
[2]IgG anti-ricin levels in sera from animals injected with human albumin were below the detection limit of 0.001 mg/ml.
[3]Data from the safety study in which the mice were exsanguinated by cardiac puncture and were necropsied for histopathological examination of the tissues.
[4]Data from the efficacy study in which the mice were bled by periorbital bleed at 1 week before aerosol challenge with ricin toxin.
[5]Standard Error of the Mean.

Figure 19:
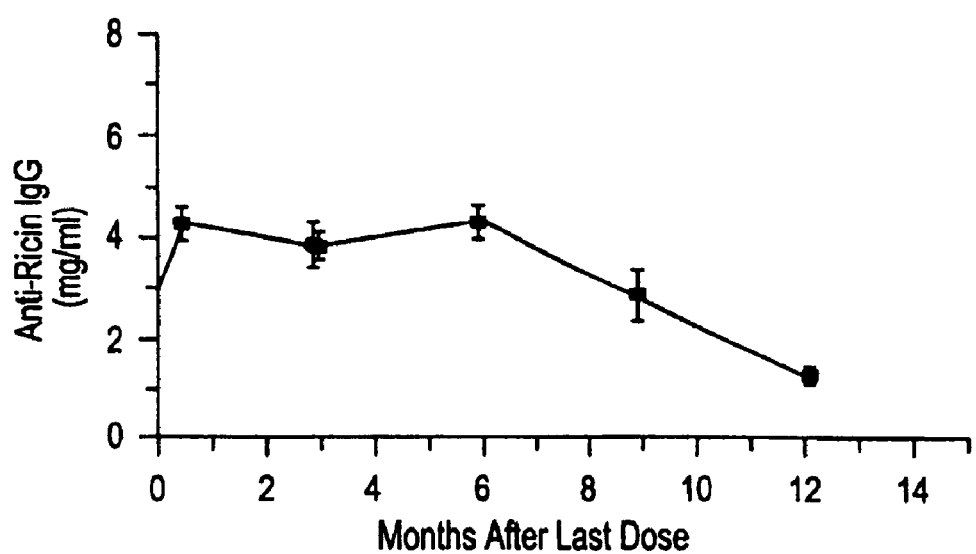
FIG. 19 shows serum anti-ricin IgG concentration at various times after last dosing with dgRTA vaccine.

Dilutions required for interpretation of the standard curve are presented for comparison to earlier studies. The mean concentration of anti-ricin toxin IgG antibodies did not change significantly during the 6 months after the last vaccination with the dgRTA vaccine. After 6 months, the concentration anti-ricin toxin IgG antibodies decreased in linear response (FIG. 19). Linear regression analysis between 6 and 18 months after last dosing indicated a half-life (t$_{½}$) of 184 days for the anti-ricin. The serum concentration of anti-ricin IgG is still supportive of the 95% survival when vaccinated mice were exposed to five LD$_{50}$ of aerosolized ricin toxin 18 months after administration of the last dose of dgRTA vaccine.

EXAMPLE 16

Production of Affinity-Purified Nonhuman Primate Anti-Ricin Toxin IgG for Development of Quantitative Immunoassays.

Two or three Rhesus monkeys will be vaccinated with three doses (0, 4, and 8 weeks) of the pilot lot of dgRTA vaccine. Two to 3 weeks after the last vaccination, the monkeys will be plasmapheresed, and purified IgG will be isolated on a Protein-A column. The IgG will be passed over an affinity column to obtain specific anti-ricin toxin IgG antibodies. This reagent will then be used to develop ELISA and in vitro neutralizing assays for the quantitative detection of anti-ricin antibody in serum from vaccinated monkeys.

EXAMPLE 17

Short- and Long-Term Efficacy of Vaccination with Two or Three Doses of dgRTA Vaccine.

A group of eight Rhesus monkeys will be vaccinated with two IM injections (0 and 4 weeks) containing 10 µg of dgRTA vaccine. Another group of eight Rhesus monkeys will be vaccinated with three IM injections (0, 4, and 8 weeks) containing 10 µg of dgRTA vaccine while a third group of two Rhesus monkeys will be dosed with three IM injections of saline. Before each vaccination or dosing, blood samples will be taken to quantify ricin antibodies and to analyze clinical chemistry and hematology parameters. Two weeks after the last vaccination/dosing, four monkeys from the two- and three-dose dgRTA vaccine groups and one monkey in the saline control group will be bled and have respiratory rate and volume measurements taken before being exposed to five $LD_{50}$ of aerosolized ricin toxin. Survivors will have blood samples taken for serology (including total IgE), hematology, and clinical chemistry and will undergo chest x-rays. At 2 and 4 weeks after exposure to the ricin toxin, two surviving monkeys, one each from the two- and three-dose groups, will be necropsied and the lungs examined for histologic lesions. The remaining four monkeys dosed with dgRTA vaccine and the one saline control monkey that were not exposed to ricin toxin will be bled monthly for anti-ricin toxin antibody concentrations and neutralizing ability. At 12 months after the last vaccination, the remaining monkeys will be challenged with aerosolized ricin toxin and survivors monitored for immunologic parameters and lung lesions. Characterization and Quantification of Particulate Formation in Reconstituted dgRTA Vaccine.

Lyophilized dgRTA vaccine will be reconstituted in bacteriostatic saline and the resulting particle removed by centrifugation. The resulting precipitate will be solubilized and characterized by SDS and CE. size exclusion HPLC, and immunoblot procedures. Quantification of particulate formation with time and varying temperature will be done by fluorescent spectrometry.

EXAMPLE 18

Evaluation of Excipients in the Reconstitution Fluid

The dgRTA vaccine is relatively stable for at least 2 years when lyophilized and stored at $\leq -15°$ C. Storage at higher temperatures results in gradual formation of particles when reconstituted at high concentrations. The formation of particles is temperature and time dependent. It is believed that the particle formation is the result of the free sulfhydryl group on the carboxyl-terminal cysteine on the dgRTA molecule forming insoluble aggregates. Also the pH of the reconstituted product is 7.0±0.3, which is the same as pI of Band A of dgRTA vaccine. Therefore, additional studies will be performed to evaluate the effect of pH and/or excipients on formation of particulates in the reconstituted dgRTA vaccine.

EXAMPLE 19

Development of Correlation of Protective Immunity

Phase 3 field trials to evaluate the efficacy of any candidate vaccine for indication of pulmonary toxicity will not be possible because inhalation is not the natural route of exposure to ricin toxin. However, there is the real threat of ricin toxin being used as a weapon of mass destruction or as a terrorist weapon. Under these circumstances, ricin toxin would most likely be aerosolized, and inhalation would lead to lung injury and edema in humans. Since vaccine efficacy against inhaled ricin toxin cannot be directly tested ethically or practically in humans, an in vitro correlate of immunity based on efficacy of the vaccine candidate in animals is being sought. It has been demonstrated that passive immunity can be induced with heterologous anti-ricin toxin IgG supporting the central role of antibody in immunity to ricin intoxication. Direct anti-ricin toxin IgG ELISA and in vitro cell neutralization tests have been developed to correlate with survival after exposure Lo lethal doses of aerosolized ricin. It is proposed that the use of the anti-ricin toxin ELISA and .neutralization tests as possible assays for an in vitro correlate of immunity be examined. A similar approach has been used for predicting protection in animals against Lyme disease (Golde et al., 1997, *Infect. Immun.* 65, 882–889).

Both active and passive immunity studies will be conducted to determine the level of antibody to ricin toxin that correlates with immunity in the mouse model. Both homologous mouse and heterologous anti-ricin toxin IgG will be used in the passive immunity studies to develop a correlate between total and neutralizing specific antibody concentrations and protection against inhaled ricin toxin. Initial, studies will be conducted in a mouse model.

What is claimed is:

1. A method of immunizing a subject from ricin intoxication by inhalation which comprises administering to the subject an amount of a deglycosylated ricin-A chain lacking about 50% of the mannose and most fucose residues present on the wild-type ricin toxin A-chain and having the ricin B-chain removed.

2. The method of claim 1, wherein the deglycosylated ricin-A chain is chemically deglycosylated by treating a ricin A-chain with a mixture of sodium metaperiodate and sodium cyanoborohydride at a pH 3.5 for 1 hour at 4° C.

3. The method of claim 1, wherein the amount is an immunogenic amount.

4. The method of claim 3, wherein the immunogenic amount is about 0.01 µg to about 100 µg per kg of the weight of the subject.

5. The method of claim 1, wherein two or more doses of the amount of the deglycosylated ricin A-chain are administered to the subject.

6. The method of claim 1, which further comprises administering an adjuvant to the subject.

7. The method of claim 1, wherein the deglycosylated ricin A-chain provides neutralizing antibodies in the subject.

8. The method of claim 1, wherein the deglycosylated ricin A-chain is in the form of an immunogenic composition, or a pharmaceutical composition.

9. The method of claim 8, wherein the immunogenic composition, or the pharmaceutical composition comprises an adjuvant.

* * * * *

UNITED STATES PATENT AND TRADEMARK OFFICE
CERTIFICATE OF CORRECTION

| | | |
|---|---|---|
| PATENT NO. | : 7,351,435 B2 | Page 1 of 1 |
| APPLICATION NO. | : 09/960315 | |
| DATED | : April 1, 2008 | |
| INVENTOR(S) | : Wannemacher et al. | |

It is certified that error appears in the above-identified patent and that said Letters Patent is hereby corrected as shown below:

On the title page, item (75), line 3, after "(US)", please add --; Ayaad W. Assaad, Frederick, MD (US)--.

Signed and Sealed this

Fifteenth Day of July, 2008

JON W. DUDAS
*Director of the United States Patent and Trademark Office*